(12) United States Patent
Oldham et al.

(10) Patent No.: US 8,169,610 B2
(45) Date of Patent: May 1, 2012

(54) DNA SEQUENCING SYSTEM

(75) Inventors: Mark Oldham, Emerald Hills, CA (US);
Eric Nordman, Palo Alto, CA (US);
Richard Reel, Hayward, CA (US); John Shigeura, Portola Valley, CA (US);
Janice Shigeura, legal representative, Portola Valley, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/153,902

(22) Filed: Jun. 6, 2011

(65) Prior Publication Data
US 2011/0236964 A1 Sep. 29, 2011

Related U.S. Application Data

(63) Continuation of application No. 12/630,683, filed on Dec. 3, 2009, now Pat. No. 7,978,326, which is a continuation of application No. 12/283,957, filed on Sep. 17, 2008, now Pat. No. 7,636,159, which is a continuation of application No. 11/644,412, filed on Dec. 22, 2006, now Pat. No. 7,428,047, which is a continuation of application No. 10/887,486, filed on Jul. 8, 2004, now Pat. No. 7,280,207, which is a continuation-in-part of application No. 10/205,028, filed on Jul. 25, 2002, now Pat. No. 6,856,390.

(60) Provisional application No. 60/307,682, filed on Jul. 25, 2001, provisional application No. 60/485,468, filed on Jul. 8, 2003, provisional application No. 60/486,112, filed on Jul. 10, 2003.

(51) Int. Cl.
*G01N 21/00* (2006.01)

(52) U.S. Cl. ....................................................... 356/344
(58) Field of Classification Search ................... 356/344
See application file for complete search history.

(56) References Cited

U.S. PATENT DOCUMENTS

| 4,660,971 A | 4/1987 | Sage et al. |
|---|---|---|
| 4,661,913 A | 4/1987 | Wu et al. |
| 4,756,427 A | 7/1988 | Göhde et al. |
| 4,786,165 A | 11/1988 | Yamamoto et al. |
| 4,832,815 A | 5/1989 | Kambara et al. |
| 4,887,721 A | 12/1989 | Martin et al. |
| 4,989,977 A | 2/1991 | North, Jr. |

(Continued)

FOREIGN PATENT DOCUMENTS

EP 0 616 211 9/1994

(Continued)

OTHER PUBLICATIONS

European Search Report, mailed Dec. 14, 2004, for European Application No. 02 75 6697 (3 pages).

(Continued)

*Primary Examiner* — Michael P Stafira

(57) ABSTRACT

An apparatus for detecting labeled beads is provided. The apparatus can include: one or more irradiation sources disposed for irradiating the one or more detection zones with radiation; at least one detector disposed for collecting charges corresponding to light signals emitted from labeled beads in the one or more detection zones, which have been excited by the radiation; and a system coupled to the at least one detector for effecting time delay integration of the charges by accumulating the charges before reading the charges at the output of the at least one detector.

13 Claims, 9 Drawing Sheets

U.S. PATENT DOCUMENTS

| | | | |
|---|---|---|---|
| 5,030,002 | A | 7/1991 | North, Jr. |
| 5,091,652 | A | 2/1992 | Mathies et al. |
| 5,141,609 | A | 8/1992 | Sweedler et al. |
| 5,173,748 | A | 12/1992 | Bilhorn |
| 5,192,412 | A | 3/1993 | Kambara et al. |
| 5,268,080 | A | 12/1993 | Kambara et al. |
| 5,277,780 | A | 1/1994 | Kambara |
| 5,314,602 | A | 5/1994 | Kambara et al. |
| 5,366,608 | A | 11/1994 | Kambara |
| 5,377,004 | A | 12/1994 | Owen et al. |
| 5,439,578 | A | 8/1995 | Dovichi et al. |
| 5,470,710 | A | 11/1995 | Weiss et al. |
| 5,529,679 | A | 6/1996 | Takahashi et al. |
| 5,582,705 | A | 12/1996 | Yeung et al. |
| 5,627,643 | A | 5/1997 | Birnbaum et al. |
| 5,636,017 | A | 6/1997 | Bruno et al. |
| 5,667,656 | A | 9/1997 | Kambara |
| 5,695,626 | A | 12/1997 | Yeung et al. |
| 5,710,628 | A | 1/1998 | Waterhouse et al. |
| 5,717,602 | A | 2/1998 | Kenning |
| 5,730,850 | A | 3/1998 | Kambara et al. |
| 5,741,411 | A | 4/1998 | Yeung et al. |
| 5,741,412 | A | 4/1998 | Dovichi et al. |
| 5,754,291 | A | 5/1998 | Kain |
| 5,759,781 | A | 6/1998 | Ward et al. |
| 5,784,157 | A | 7/1998 | Gorfinkel et al. |
| 5,790,727 | A | 8/1998 | Dhadwal et al. |
| 5,833,826 | A | 11/1998 | Nordman |
| 5,833,827 | A | 11/1998 | Anazawa et al. |
| 6,005,663 | A | 12/1999 | Waterhouse et al. |
| 6,017,434 | A | 1/2000 | Simpson et al. |
| 6,084,667 | A | 7/2000 | Melman et al. |
| 6,110,683 | A | 8/2000 | Reynolds et al. |
| 6,140,048 | A | 10/2000 | Müller et al. |
| 6,211,955 | B1 | 4/2001 | Basiji et al. |
| 6,249,341 | B1 | 6/2001 | Basiji et al. |
| 6,406,848 | B1 | 6/2002 | Bridgham et al. |
| 6,473,176 | B2 | 10/2002 | Basiji et al. |
| 6,524,860 | B1 | 2/2003 | Seidel et al. |
| 6,529,275 | B2 | 3/2003 | Amirkhanian et al. |
| 6,532,061 | B2 | 3/2003 | Ortyn et al. |
| 6,549,275 | B1 | 4/2003 | Cabuz et al. |
| 6,563,583 | B2 | 5/2003 | Ortyn et al. |
| 6,580,504 | B1 | 6/2003 | Ortyn et al. |
| 6,583,865 | B2 | 6/2003 | Basiji et al. |
| 6,608,680 | B2 | 8/2003 | Basiji et al. |
| 6,608,682 | B2 | 8/2003 | Ortyn et al. |
| 6,618,140 | B2 | 9/2003 | Frost et al. |
| 6,654,505 | B2 | 11/2003 | Bridgham et al. |
| 6,671,044 | B2 | 12/2003 | Ortyn et al. |
| 6,749,735 | B1 | 6/2004 | Le Febre |
| 6,763,149 | B2 | 7/2004 | Riley et al. |
| 6,778,263 | B2 | 8/2004 | Ortyn et al. |
| 6,806,052 | B2 | 10/2004 | Bridgham et al. |
| 6,831,994 | B2 | 12/2004 | Bridgham et al. |
| 6,856,390 | B2 | 2/2005 | Nordman et al. |
| 6,875,973 | B2 | 4/2005 | Ortyn et al. |
| 6,934,408 | B2 | 8/2005 | Frost et al. |
| 6,969,488 | B2 | 11/2005 | Bridgham et al. |
| 6,975,400 | B2 | 12/2005 | Ortyn et al. |
| 7,009,651 | B2 | 3/2006 | Ortyn et al. |
| 7,057,732 | B2 | 6/2006 | Jorgenson et al. |
| 7,190,832 | B2 | 3/2007 | Frost et al. |
| 7,265,833 | B2 | 9/2007 | Oldham et al. |
| 7,280,207 | B2 | 10/2007 | Oldham et al. |
| 7,282,370 | B2 | 10/2007 | Bridgham et al. |
| 7,428,047 | B2 | 9/2008 | Oldham et al. |
| 7,450,229 | B2 | 11/2008 | Ortyn et al. |
| 7,522,758 | B2 | 4/2009 | Ortyn et al. |
| 7,610,942 | B2 | 11/2009 | Harui et al. |
| 7,636,159 | B2 | 12/2009 | Oldham et al. |
| 7,978,326 | B2 | 7/2011 | Oldham et al. |
| 2002/0071121 | A1* | 6/2002 | Ortyn et al. .......... 356/419 |
| 2002/0127603 | A1 | 9/2002 | Basiji et al. |
| 2002/0146734 | A1 | 10/2002 | Ortyn et al. |
| 2004/0165256 | A1 | 8/2004 | Teng et al. |
| 2006/0246481 | A1 | 11/2006 | Finch et al. |
| 2006/0257884 | A1 | 11/2006 | Brawley et al. |
| 2007/0146873 | A1 | 6/2007 | Ortyn et al. |
| 2008/0317325 | A1 | 12/2008 | Ortyn et al. |
| 2009/0202130 | A1 | 8/2009 | George et al. |
| 2010/0103416 | A1 | 4/2010 | Oldham et al. |

FOREIGN PATENT DOCUMENTS

| | | |
|---|---|---|
| WO | WO 95/11961 | 5/1995 |
| WO | WO 95/23348 | 8/1995 |
| WO | WO 97/19342 | 5/1997 |
| WO | WO 98/12536 | 3/1998 |
| WO | WO 00/25113 | 5/2000 |
| WO | WO 02/17219 | 2/2002 |
| WO | WO 02/23163 A1 | 3/2002 |
| WO | WO 02/059577 A2 | 8/2002 |
| WO | WO 03/010524 A1 | 2/2003 |

OTHER PUBLICATIONS

International Search Report, mailed Dec. 15, 2004, for PCT/US2004/022203 (3 pages).

International Search Report, dated Jun. 15, 2005, for PCT/US2004/022202 (5 pages).

Hoy, Terry, *Cell Sorting: Principles*, http://www.uwcm.ac.uk/study/medicine/haematology/cytonetuk/documents/sort.pps, Printed Apr. 14, 2004.

Richard T. Reel, *Camera Lens Spectrograph Optics Design for MegaGUT*, pp. 1-42, (Jan. 16, 1997).

Milos V. Novotny, Capillary electrophoresis, *Current Opinion in Biotechnology*, vol. 7, pp. 29-34 (1996).

Simpson, et al., A transmission imaging spectrograph and microfabricated channel system for DNA analysis, *Electrophoresis 2000*, vol. 21, pp. 135-149 (2000).

Ross, et al., High Sensitivity is Key to CE Detection Boost, *Today's Chemist at Work*, Vo. 6(8), pp. 31-32, 34 and 36, (Sep. 1997).

Kotichka, et al., High Speed Automated DNA Sequencing in Ultrathin Slab Gels, *Bio/Technology*, vol. 10, pp. 78-81, (Jan. 1992).

Karger, et al., Multiwavelength fluorescence detection for DNA sequencing using capillary electrophoresis, *Nucleic Acids Research*, vol. 19, No. 18, pp. 4955-4962, (Jul. 29, 1991).

Genome Sequencing Center, Washington University School of Medicine St. Louis, MO USA, *EST & GSS Projects*, http://genome.wustl.edu/est/est_general/trace_intro.html., (Monday, Mar. 26, 2001).

Kevin Altria, Capillary electrophoresis, *Royal Society of Chemistry*, 7 Sheets, (2000).

Paul D. Grossman, Factors Affecting the Performance of Capillary Electrophoresis Separations: Joule Heating, Electroosmosis, and Zone Dispersion, *Academic Press, Inc.*, pp. 3, 24, 28, and 38, (1992).

Brochure, Charge-Coupled Devices for Quantitative Electronic Imaging, *Photometrics, Ltd*, pp. 1-3, and 6-17, (1992).

Sweedler, et al., Fluorescence Detection in Capillary Zone Electrophoresis Using a Charge-Coupled Device with Time-Delayed Integration, *Analytical Chemistry*, vol. 63, No. 5, pp. 496-502, (Mar. 1, 1991).

F. Sanger, et al., DNA Sequencing with Chain Terminating Inhibitors, 74 *Proc. Nat. Acad. Sci. USA*, 5463, (1977).

Lloyd M. Smith, et al., Fluorescence detection in automated DNA sequence analysis, 321 *Nature* 674, (1986).

Lloyd M. Smith, et al., The Future of DNA sequencing, 262 *Science* 530, (1993).

L. Kricka, Nonisotopic DNA Probe Techniques, *Academic Press*, San Diego, pp. 3-28, (1992).

Bronstein, *Anal. Biochemistry*, 219:169-81 (1993).

*Charge-Coupled Devices for Quantitative Electronic Imaging*, Photometrics Ltd., (1992).

\* cited by examiner

Fig. 4
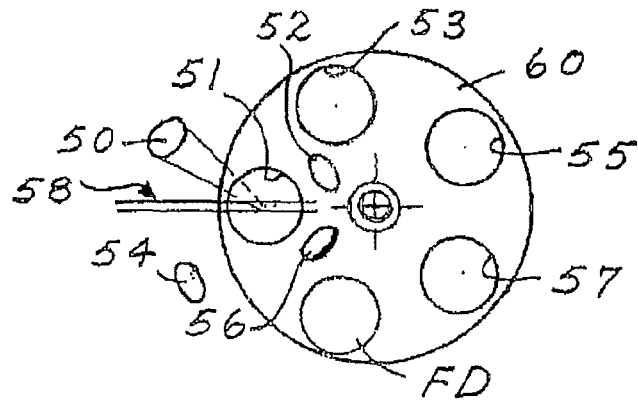
Fig. 5a                Fig. 5b
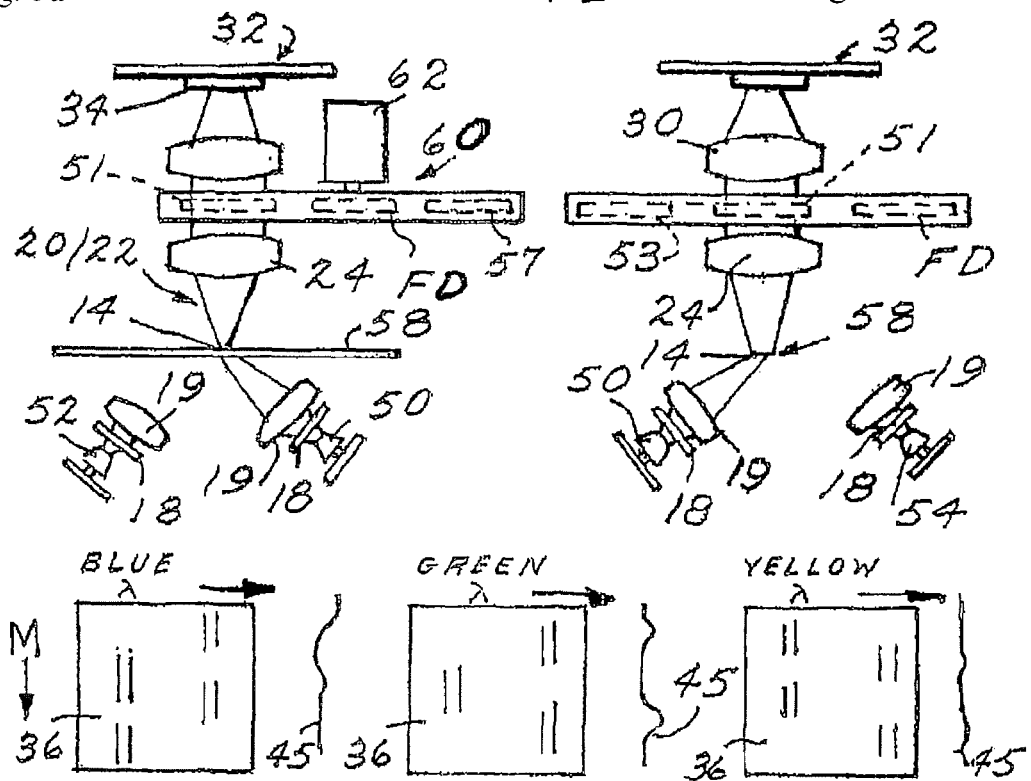
Fig. 6a        Fig. 6b        Fig. 6c
Fig. 6d        Fig. 6e Fig. 10
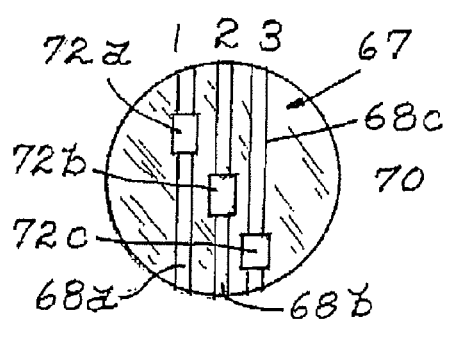
Fig. 11
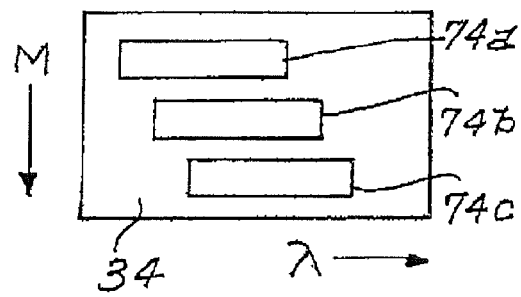
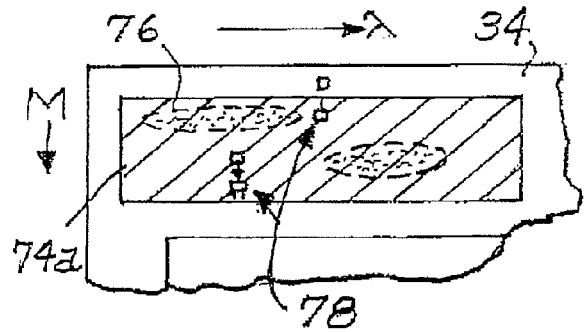
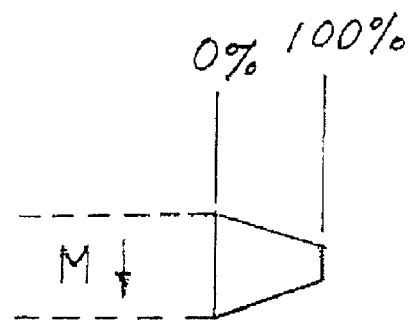
Fig. 12a
Fig. 12b

DNA SEQUENCING SYSTEM

CROSS-REFERENCE TO RELATED APPLICATIONS

This application is a continuation of U.S. patent application Ser. No. 12/630,683, filed on Dec. 3, 2009, which is a continuation of U.S. patent application Ser. No. 12/283,957, filed on Sep. 17, 2008 (now U.S. Pat. No. 7,636,159), which is continuation of Ser. No. 11/644,412, filed Dec. 22, 2006 (now U.S. Pat. No. 7,428,047), which is a continuation of U.S. patent application Ser. No. 10/887,486 filed on Jul. 8, 2004 (now U.S. Pat. No. 7,280,207), which is a continuation-in-part of U.S. patent application Ser. No. 10/205,028 filed on Jul. 25, 2002 (now U.S. Pat. No. 6,856,390), which claims a benefit from U.S. Provisional Patent Application No. 60/307,682 filed on Jul. 25, 2001, and U.S. patent application Ser. No. 10/887,486 (now U.S. Pat. No. 7,280,207) also claims benefit under 35 U.S.C. §119(e) to U.S. Provisional Patent Application No. 60/485,468, filed Jul. 8, 2003, and application Ser. No. 10/887,486 also claims benefit under 37 U.S.C. §119(e) to U.S. Provisional Patent Application No. 60/486,112, filed on Jul. 10, 2003. Each of the above-identified patents and patent applications are incorporated herein in their entireties by reference. U.S. patent application Ser. No. 10/805,096, filed Mar. 19, 2004, to Reel et al., is also incorporated herein in its entirety by reference.

FIELD

The present teachings relate to a detection method useful in a flow cytometry system.

BACKGROUND

Well-known examples of biopolymer analysis using DNA sequencing are taught, for example, in F. Sanger et al., *DNA Sequencing with Chain Terminating Inhibitors*, 74 Proc. Nat. Acad. Sci. USA 5463 (1977); Lloyd M. Smith et al., *Fluorescence defection in automated DNA sequence analysis*, 321 Nature 674 (1986); and Lloyd M. Smith, *The Future of DNA Sequencing*, 262 Science 530 (1993). These and all other publications and patents cited herein are incorporated herein in their entireties by reference.

The use of sources of irradiation other than lasers for the excitation of marker compounds provides many advantages. Although the use of light emitting diodes (LEDs) for generating fluorescence in dye molecules is taught, for example, in U.S. Pat. Nos. 6,005,663 and 5,710,628, the contents of which are incorporated herein in their entireties by reference, the use of LEDs in such electrophoretic methods typically results in low signal strengths and marginal detection sensitivity. The low signal strength can impair adequate detection of marker compounds.

An electrophoretic and/or other separation apparatus and method that includes a cost-effective and convenient source of irradiation and that does not compromise sensitivity or resolution would be desirable, especially in a multiple-channel electrophoretic or flow cytometry system.

SUMMARY

According to various embodiments, an apparatus for detecting analytes in a sample containing at least one analyte is provided. The apparatus can include: a flow cytometry system including a channel having one or more detection zones; one or more irradiation sources disposed for irradiating the one or more detection zones with non-coherent radiation; at least one detector disposed for collecting at least one charge corresponding to an emission beam emitted from the one or more detection zones, the at least one detector having at least one output; modulating optics disposed between the irradiation source and the at least one detector; and a time delay integration system coupled to the at least one detector for effecting time delay integration of the at least one charge by accumulating the at least one charge before reading the at least one charge at the output of the at least one detector. The time delay integration system can accumulate the at least one charge by moving, relative to one another, the modulating optics and the channel.

According to various embodiments, an apparatus for detecting analytes in a sample is provided. The apparatus can include: a flow cytometry system including a channel having at least one detection zone; one or more irradiation sources disposed for irradiating the at least one detection zone with radiation; at least one detector disposed for collecting at least one charge corresponding to an emission beam emitted from the at least one detection zone, each detector of the at least one detector having an output; modulating optics disposed between the irradiation source and the at least one detector; and a time delay integration system coupled to the at least one detector for effecting time delay integration of the at least one charge by accumulating the at least one charge before reading the at least one charge at the output of the at least one detector. The time delay integration system can accumulate the at least one charge by moving, relative to one another, the modulating optics and the channel. The one or more irradiation sources can include a solid state laser or a micro-wire laser.

According to various embodiments, an apparatus for sorting analytes in a sample containing at least one detectable analyte is provided. The apparatus can include: a channel having one or more detection zones; one or more irradiation sources disposed for irradiating the one or more detection zones with non-coherent radiation; at least one detector disposed for collecting light signals emitted from the at least one detectable analyte in the one or more detection zones excited by the radiation, the at least one detector having an output; a time delay integration system coupled to the at least one detector for effecting the time delay integration of at least one charge on the at least one detector, corresponding to the light signals by accumulating the at least one charge before reading the at least one charge at the output of the at least one detector; and a sorting system capable of directing the flow of at least one detectable analyte.

According to various embodiments, a method for sorting analytes in a sample containing at least one detectable analyte is provided. The method can include providing a channel-defining-member defining a channel therein having at least one detection zone. The method can include separating a sample containing at least one detectable analyte moving through the channel. The method can include irradiating the at least detection zone using one or more irradiation sources generating radiation of such wavelength as to thereby excite the at least one detectable analyte and cause the at least one detectable analyte to emit light signals indicative of the at least one detectable analyte. The method can include detecting the light signals produced by the at least one detectable analyte by collecting the light signals on at least one detector to produce charges on the at least one detector corresponding to the light signals. The method can include modulating light between the one or more irradiation sources and the at least one detector using modulating optics. The method can include effecting a time delay integration of the light signals within the at least one detector by accumulating at least one charge within the at least one detector corresponding to light signals associated with the at least one detectable analyte during an integration time of the at least one detectable analyte moving across the at least one detection zone. The accumulation can be effected by moving, relative to one another, the modulating optics and the channel. The method can include reading the at least one accumulated charge. The method can include sorting a detectable analyte of the sample based on the reading of the at least one accumulated charge. The sorting can be performed with a flow cytometry apparatus and method, for example.

According to various embodiments, an apparatus is provided that can include a sorting system for separating each of a plurality of detected analytes into respective collections of analytes, and which uses a time-delay integration detection system to detect the analytes. The sorting system can include a motive force for directing the analyte to an analyte collector. The collector can include a dish, channel, capillary tube, beaker, or other device capable of retaining the analyte. The motive force can act on the analyte, on the collector, or both. The motive force can be an electro-kinetic force, a mechanical force, an electric field gradient, a vacuum, or a combination thereof.

According to various embodiments, the apparatus can include a separation device for directing a detected component to flow along one or more pathways, for example, by electrokinetic movement or mechanical movement of the detected component or by such movement of the pathway for receiving the detected component. The apparatus can further include a system coupled to the at least one detector for effecting time delay integration of the charges on the at least one detector corresponding to the light signals by accumulating the charges before reading the charges at the output of the at least one detector.

According to various embodiments, the flow cytometry system can include an electric field gradient source. The one or more irradiation sources can include one or more light emitting diodes. The one or more light emitting diodes can include one or more organic light emitting diodes. The modulating optics can include a relay lens system comprising a collimating lens and a re-imaging lens. The modulating optics can include a conditioning filter disposed between the one or more irradiation sources and the one or more detection zones. The conditioning filter can include a longpass filter, a shortpass filter, a multi-notch filter, a beamsplitter, or a combination thereof. The modulating optics can include a focusing lens disposed between the conditioning filter and the one or more detection zones. The modulating optics can include a transmission grating disposed between the focusing lens and the re-imaging lens. The modulating optics can include a filter disposed between the one or more detection zones and the at least one detector for filtering through only the emission beam. The filter can include a longpass filter, a shortpass filter, a multi-notch filter, a bandpass filter, a beam splitter, or a combination thereof.

According to various embodiments, the apparatus can include a sample containing whole cells. The apparatus can include a sample containing the at least one analyte labeled with at least one marker. The at least one marker can include a dye marker, a fluorescing dye, a free-floating dye, a reporter dye, a probe dye, an intercalating dye, a quantum dot, a molecular beacon, a quantum dot media, a quantum dot bead, a dye-labeled bead, a dye attached to an analyte associated with a bead, or a combination thereof. The modulating optics can include at least one conditioning filter for each irradiation source of the one or more irradiation sources, each respective conditioning filter being effective for substantially blocking predetermined excitation wavelengths to produce conditioned light. The predetermined excitation wavelengths of each marker can be without conflict with the excitation spectra of each other marker. The modulating optics can include at least one long pass filter and at least one bandpass filter for each irradiation source of the one or more irradiation sources, each of the at least one long pass filter and each of the at least one bandpass filter being effective for letting through, substantially exclusively, predetermined wavelengths of light from the one or more detection zones corresponding to a portion of the wavelengths of the light signals emitted by the at least one marker, to thereby produce filtered light.

According to various embodiments, the apparatus can include a separating device. The separating device can include a plurality of separation regions. The one or more irradiation sources can include a single light emitting diode. The apparatus can include a device capable of spectrally distributing the light signals to thereby produce spectrally distributed light. The one or more irradiation sources can include a plurality of light emitting diodes each emitting light in a respective predetermined frequency range, and the respective bandpass filter can include a plurality of bandpass filters each associated with a respective one of the plurality of light emitting diodes, each respective bandpass filter being effective for letting through, substantially exclusively, predetermined wavelengths of light from the one or more detection zones corresponding to a portion of the wavelengths of the light signals emitted by each marker of the at least one marker to thereby produce filtered light.

According to various embodiments, the apparatus can include an offset system for spatially offsetting, on the at least one detector, at least one image for each conditioning filter by a predetermined amount. The offset system can include a plurality of offset mechanisms, each associated with a respective one of the conditioning filters. Each offset mechanism can include one or more of a glass plate, a grating, a mirror, or a combination thereof. The offset system can be adapted to effect a translational movement of at least one of the at least one detector, the modulating optics, and the one or more detection zones, with respect to one another, for spatially offsetting the at least one image by a second predetermined amount.

According to various embodiments, the apparatus can include a filter wheel. The bandpass filters can be disposed on the filter wheel, with each respective bandpass filter further being selectively positionable with respect to the one or more detection zones for filtering light emitted from the one or more detection zones by the at least one marker associated with each respective bandpass filter.

According to various embodiments, the time delay integration system can control the at least one detector to read the at least one accumulated charge on a frame by frame basis, each frame corresponding to the at least one accumulated charge on the at least one detector during an integration time and produced by the conditioned light through each conditioning filter. The time delay integration system can control the at least one detector to read the at least one accumulated charge on a continuous basis. The at least one detector can include a two-dimensional charge-coupled device. The one or more irradiation sources can include a plurality of light emitting diodes adapted to simultaneously irradiate the one or more detection zones, each of the light emitting diodes illuminating a separate one of the one or more detection zones. The apparatus can include masks to selectively mask the channel such that the light signals from the respective one or more detection zones can be distinct. The time delay integration system can include a system coupled to the modulating optics for moving the modulating optics relative to the channel at a speed that is synchronized to a movement of the at least one analyte across the one or more detection zones. The time delay integration system can include a system coupled to the channel for moving the channel relative to the modulating optics at a speed that is synchronized to a movement of the at least one analyte across the one or more detection zones.

According to various embodiments, the apparatus can include a sorting system including one or more collection channels and a controller for controlling a motive force for each collection channel. The sorting system can sort each analyte into a respective one of the one or more collection channels. The motive force can include an electrokinetic force, a mechanical force, a production of electric field gradient, a switchable electric field, vacuum, a stream of air, or a combination thereof. The controller can include more than one controller, each controller associated with a respective collection channel.

It is to be understood that both the foregoing general description and the following detailed description are exemplary and explanatory only. The accompanying drawings, which are incorporated in and constitute a part of this application, illustrate several exemplary embodiments and, together with the instant description, serve to explain the principles of the present teachings.

BRIEF DESCRIPTION OF DRAWINGS

Various embodiments of the present teachings are exemplified in the accompanying drawings. The teachings are not limited to the embodiments depicted, and include equivalent structures and methods as set forth in the following description and known to those of ordinary skill in the art. In the drawings:

FIG. 4 is a schematic, front-elevational view of an electrophoresis arrangement for the sequential use of multiple-color irradiation sources along with filters on a filter wheel, according to various embodiments;

FIG. 5a is a schematic, top-plan view of the arrangement of FIG. 4;

FIG. 5b is a schematic, side-elevational view of the arrangement of FIG. 4;

FIGS. 6a through 6e are respective schematic views of images produced on the detector array of a detector, each image corresponding to light signals filtered through a respective filter on the filter wheel of FIG. 4;

FIG. 9a is a graph of relative excitation intensity versus wavelength for a pair of LEDs used in another embodiment, the LEDs can be of different colors and can be used to irradiate the detection zone simultaneously;

FIG. 9b is a graph showing percent transmission versus wavelength for a conditioning filter used to condition the light from the LEDs of FIG. 9a;

FIG. 9c is a graph showing percent transmission versus wavelength for a bandpass filter used to filter light signals produced by markers excited by the light from the LEDs of FIG. 9a;

FIG. 9d is a graph showing relative emission intensity versus wavelength for the light filtered through the bandpass filter of FIG. 9c;

FIG. 10 is a schematic, top-plan view of an irradiation zone showing three channels having been selectively masked to present respective windows according to another embodiment;

FIG. 11 is a schematic view of a detector array, the detector array having been separated into respective frames for use with light signals emitted from the respective windows of the channels in FIG. 10;

FIG. 12a is a partially cut away view of one of the frames of the detector array shown in FIG. 11;

FIG. 12b is a graph showing percent integration per pixel throughout the width of the frame as shown in FIG. 12a;

It is to be understood that both the foregoing general description and the following detailed description are exemplary and explanatory only and are intended to provide a further explanation of the various embodiments of the present teachings.

DESCRIPTION

The analytes of interest can be detected on the basis of an intrinsically detectable signal, or may be derivatized with a label which confers a desired type of detectability. Various methods for labeling analytes with detectable moieties are well known in the art, such as excitable reporters, radioactive isotopes, fluorescent dyes, spin labels, chemiluminescent compounds and the like to stimulate detectable emission indicative of the nature of the analyte. When the analyte is a polynucleotide, labeling by hybridization with a labeled probe can also be used. The analyte can be labeled with a dye marker, a fluorescing dye, a free-floating dye, a reporter dye, a probe dye, an intercalating dye, a quantum dot, a molecular beacon, a linear probe, a quantum dot media, a quantum dot bead, a dye-labeled bead, a dye attached to an analyte associated with a bead, or a combination thereof.

While the present teachings are related more generally to separation devices including a time-delay integration detection capability or method, the teachings can be exemplified with reference to the electrophoretic separation system described herein with reference to FIGS. 1-12b. Although the detectable components described herein are referred to as analytes or analyte bands, it should be noted that such analytes can include whole cells, whole blood cells, nucleic acid sequences, and other biological samples.

Exemplary analytes can include nucleic acids, both single and double stranded, proteins, carbohydrates, viruses, cells, whole cells, organelles, organic polymers, other biological samples, particles, labeled media, labeled beads, and the like. The analytes can include biomolecules, for example, cells, proteins, DNA, RNA, polynucleotides, polypeptides, polysaccharides, and small molecule analytes. According to various embodiments, the analyte can be a selected-sequence polynucleotide, and an analyte-specific reagent including a sequence-selective reagent for detecting the polynucleotide can be associated with the polynucleotide. Polynucleotide analytes can be detected by any suitable method, for example, polymerase chain reaction, ligase chain reaction, oligonucleotide ligation assay, hybridization assay, antibody assay, affinity assay, or streptavidin/biotin assay.

Figure 1:
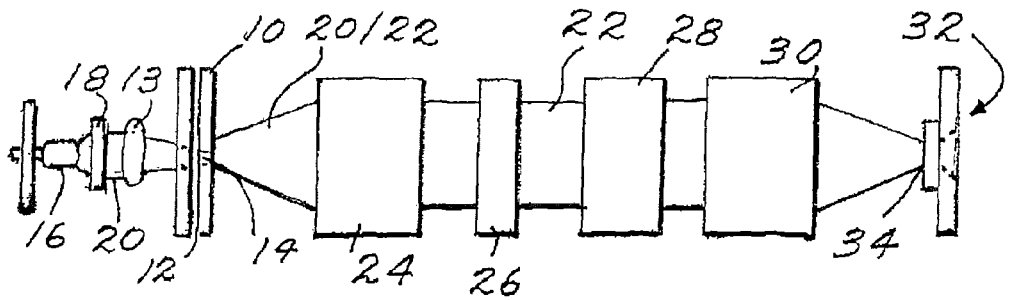
FIG. 1 is a schematic, side-elevational view of an electrophoresis arrangement showing a channel-defining member in cross-section, according to various embodiments.

FIG. 1 shows an exemplary embodiment of an electrophoresis device. As depicted in FIG. 1, the arrangement can include a channel-defining member 10 defining a channel 12 therein for the migration of an analyte sample. The channel-defining member 10 can include a cover plate with or without grooves, an etched plate defining one or more capillary sized grooves therein, or one or more capillary tubes. According to various embodiments, the channel-defining member can be an etched plate having a plurality of channels or grooves, or the channel-defining member can include a plurality of capillary tubes. The use of a plurality of channels can allow a large number of analyte samples to be measured simultaneously in order to increase throughput. As is well known, for electrophoresis to occur, opposing ends of channel-defining member 10, such as an electrophoretic plate or capillary tube, can be placed in contact with corresponding electrodes connected to a power supply for generating an electric field across the plate or tube. This field can cause the analyte to migrate from a loading site (not shown) for the plate or tube arrangement of the channel-defining member 10, toward a detection site or detection zone 14. The detection zone can encompass that zone on the channel that is irradiated by an irradiation source to excite markers, such as dye markers, used to label analytes in the sample.

An example of a marker compound can be a dye marker. Any suitable marker, such as, for example, a fluorophore, can be used. Fluorophores useful according to various embodiments can include those that can be coupled to organic molecules, particularly proteins and nucleic acids, and that can emit a detectable amount of radiation or light signal in response to excitation by an available excitation source. Suitable markers can encompass materials having fluorescent, phosphorescent, and/or other electromagnetic radiation emissions. Irradiation of the markers can cause them to emit light at varying frequencies depending on the type of marker used.

One class of markers provides signals for the detection of labeled extension and amplification products by fluorescence, chemiluminescence, or electrochemical luminescence (Kricka, L. in *Nonisotopic DNA Probe Techniques*, Academic Press, San Diego, pp. 3-28 (1992)). Chemiluminescent labels can include 1,2-dioxetane compounds (U.S. Pat. No. 4,931, 223; and Bronstein, Anal. Biochemistry 219:169-81 (1994)). Fluorescent dyes useful for labeling probes, primers, and nucleotide 5'-triphosphates include fluoresceins, rhodamines (U.S. Pat. Nos. 5,366,860; 5,936,087; and 6,051,719), cyanines (Kubista, WO 97/45539), and metal porphyrin complexes (Stanton, WO 88/04777). Fluorescent reporter dyes include xanthene compounds such as fluoresceins I and rhodamines II:

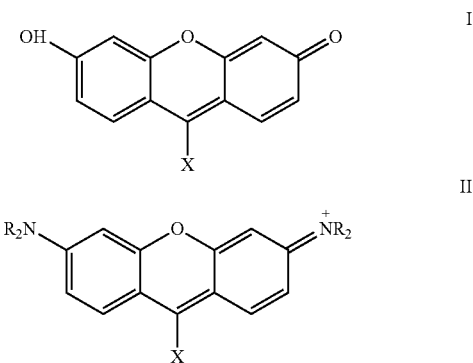

The ring positions of I and II above can be substituted. The amino R groups of II can be substituted. The substituents can include covalent attachments to the primers, probes, or nucleotides. Examples of formulae I and II include wherein X can be phenyl substituted with carboxyl, chloro, and other groups, for example, as described in U.S. Pat. Nos. 5,847,162; 6,025, 505; 5,674,442; 5,188,934; 5,885,778; 6,008,379; 6,020,481; and 5,936,087, which are incorporated herein in their entireties by reference, and wherein X can be hydrogen, for example, as described in U.S. Pat. No. 6,051,719, which is incorporated herein in its entirety by reference.

According to various embodiments, an optical instrument can be provided that includes a light source arranged to emit an excitation wavelength or wavelength range toward a region capable of retaining a sample, such that a fluorescent dye, if present in the region, can be caused to fluoresce. The light source can provide excitation wavelength ranges that correspond to respective excitation wavelength ranges of a plurality of fluorescent dyes. A detector capable of detecting an emission wavelength emitted from a fluorescing dye can be used to determine the absence or presence of a component associated with the dye. For example, the dyes can include intercalating dyes, reporter dyes, free-floating dyes, and the like.

According to various embodiments, PCR dyes can be used that only fluoresce when bound to a target molecule. Nucleic acid sequence amplification dyes can also be attached to probes that also are connected to quenchers, and the action of nucleic acid sequence amplification enzymes will disassemble the dye-probe-quencher molecule causing the dye to increase its fluorescence. According to various embodiments, nucleic acid sequence amplification can be performed using a variety of methods, for example, polymerase chain reaction (PCR), isothermal amplification reaction, well known in the art. When a PCR procedure is used, for example, the number of unquenched dye molecules doubles with every thermal cycle. Fluorescing dyes are well known in the art, and any of a plurality of fluorescent dyes having various excitation wavelengths can be used. Examples of such dyes include, but are not limited to, Rhodamine, Fluoroscein, dye derivatives of Rhodamine, dye derivatives of Fluoroscein, 5-FAM™, 6-carboxyfluorescein (6-FAM™), VIC™, hexachloro-fluorescein (HEX™), tetrachloro-fluorescein (TET™), ROX™, and TAMRA™. Dyes or other identifiers that can be used include, but are not limited to, fluorophores and phosphorescent dyes. Dyes can be used in combinations of two, three, four, or more dyes per sample. According to various embodiments, the family of 5-FAM™ 6-FAM™, VIC™, TET™, and/or ROX™ dyes can be used to indicate the presence of sample components.

According to various embodiments, various detectable markers can be used, in addition or in alternate, to dyes. Markers can include, for example, fluorescing dyes, free-floating dyes, reporter dyes, probe dyes, intercalating dyes, and molecular beacons. Dyes that fluoresce when integrated into DNA can be intercalating dyes. Other dyes known as "reporter" dyes can attached to the ends of "probes" that have "quenchers" on the other end. A nucleic acid sequence amplification reaction, for example, PCR, can result in the disassembly of the Dye-Probe-Quencher molecule, so the reporter dye can emit an increased amount of fluorescence. Reporter dyes are not attached in any way to the sample. Free floating dyes can be floating freely in solution. Other fluorescing markers well know in the art can be utilized. According to various embodiments, molecular beacons can be single-stranded molecules with hairpins that preferentially hybridize with an amplified target to unfold. According to various embodiments, quantum dots can be used as markers also.

In the embodiment shown in FIG. 1, an irradiation source is provided that emits light in a given frequency range, such as, for example, a light emitting diode (LED) 16. It can be to be noted that, in the instant description, the source of light can be any of a variety of light sources. According to various embodiments, the light can have a frequency of about 660 nm or lower. The irradiation source can be, for example, an LED, an organic LED, a non-coherent light source as known to those skilled in the art, a solid state laser, a microwire laser, or a combination thereof. As used herein, the terms "irradiation source," "light source," "excitation source," "LED," or the like can include single or multiple sources of irradiation, including LED flood light arrays. As used herein, "LED" can refer to an LED, an OLED, or multiplicities thereof. Further, according to various embodiments, the "LED" can include coherent irradiation sources, for example, a solid state laser source or a micro-wire laser source.

According to various embodiments, the light from the LED can be modulated by an excitation modulating optics system before reaching the detector zone 14. The excitation modulating optics system can include, as shown, a conditioning filter 18, the role of which can be to substantially block predetermined ranges of wavelengths of light emitted by the LED. The predetermined ranges can correspond to wavelengths of light that can overlap with the emission spectra of the markers being used. According to various embodiments, the conditioning filter can let through only light in the wavelength range of the excitation light of one or more of the markers. Any given LED can emit excitation light in a spectral range. The range of wavelengths of the excitation light in turn can excite markers to emit light signals within a given spectral range in the detection zone. For the detection of light signals from the detection zone, that portion of the excitation light that would be in the same wavelength range as some or all of the light signals emitted from the detection zone can be blocked. The light passing through the conditioning filter 18 is conditioned light 20, as seen in FIG. 1.

The excitation modulating optics system can further include a focusing optical system 19. The conditioned light 20 can be focused by focusing optical system 19 to irradiate the analyte sample and corresponding markers in the detection zone 14. The thus irradiated marker or markers can turn emit light signals, such as through fluorescence, at frequencies specific to the irradiated marker, so as to present a peak intensity. For example, a dye excited by yellow light can have a fluorescence emission peak intensity at 610 nm corresponding to the orange portion of the spectrum. A peak intensity of about 460 nm can be associated with the blue portion of the spectrum, and a peak intensity of about 660 nm can be associated with the red portion of the spectrum. By way of example, ROX, a known dye marker, can be best excited at 590 nm. ROX can be excited by an LED emitting radiation at 590 nm.

The device of FIG. 1 can include a collection modulating optics system that can include a collimating optical system 24, a wide bandpass filter 26, a transmission grating 28, and a re-imaging optical system 30. Emitted light 22 from the detection zone 14, and, in addition, conditioned light 20 passing through the detection zone 14, can be collimated by a first optical component or system 24. The light from the detection zone can include the emitted light 22 and a portion of the conditioned light 20 passing through the detection zone. Alternatively, the excitation light can be brought in at an angle with respect to the detection zone such that most of the conditioned light passing through the detection zone is not collected by the collimating optical system 24. This reduces the excitation light that might be rejected. However, such an alternative arrangement also decreases the level of excitation light that hits the detection zone 14. It can be, nevertheless, possible to establish a compromise between irradiation angle and level of excitation light, as readily recognizable by those skilled in the art.

The light 20 and 22 from the detection zone 14 can be collimated by collimating optical system 24. What is meant in the context of various embodiments by collimation is any reduction in the propagation angle of the light being collimated. According to various embodiments, the reduction in the propagation angle of the light being collimated can result in a propagation angle between about 20 degrees and about 0 degrees.

According to various embodiments, a long pass filter, or, in the alternative, a wide bandpass filter 26, can be used for letting through, substantially exclusively, predetermined wavelengths of light from the detection zone corresponding to a portion of wavelengths of the light signals emitted by an associated marker. The portion of the wavelengths of the light signals can include, for example, all of the light signals, or it can include, for each marker, a range of wavelengths of the light signals, such as a range of wavelengths about the peak intensity of the light signals. As an example, a wide bandpass filter can block wavelengths of light outside of the range of from about 500 nm to about 700 nm, thereby letting through only light that corresponds very specifically to the light emitted by the markers, that is, corresponding to emitted light 22. Thereafter, emitted light 22 can be spectrally distributed by a transmission grating 28 and refocused by re-imaging optical system 30 onto an array 34 of solid-state detectors, or detector array 34. The excitation modulating optics system and the collection modulating optics system are hereinafter collectively referred to as "the modulating optics system" or "modulating optics." According to various embodiments, the array of solid-state detectors can include the photo-detecting surface of the parallel register of a charge-coupled device (CCD) 32. As shown in FIG. 1, the image produced by refocusing emitted light 22 can be projected onto the detector array 34 of the CCD, producing a pattern of charge in proportion to the total integrated flux incident on each pixel of the parallel register, as is well known in the art.

According to various embodiments, at least one of the excitation beam pathway and the emission beam pathway can pass through a lens system, for example, a ball lens. The modulating optics system can include the lens system. For example, the excitation beam pathway and/or the emission beam pathway can pass through a lens system as described in U.S. patent application Ser. No. 10/805,096, filed Mar. 19, 2004, which is incorporated herein in its entirety by reference. The modulating optics system can include or be separate from a lens system as described in U.S. patent application Ser. No. 10/805,096.

Figure 2:
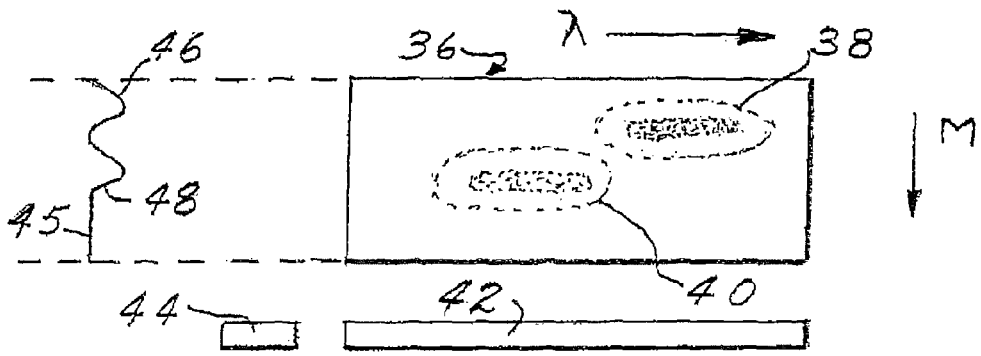
FIG. 2 is a schematic view of an image produced on a detector array of a detector at a time t using the arrangement of FIG. 1.
Figure 3:
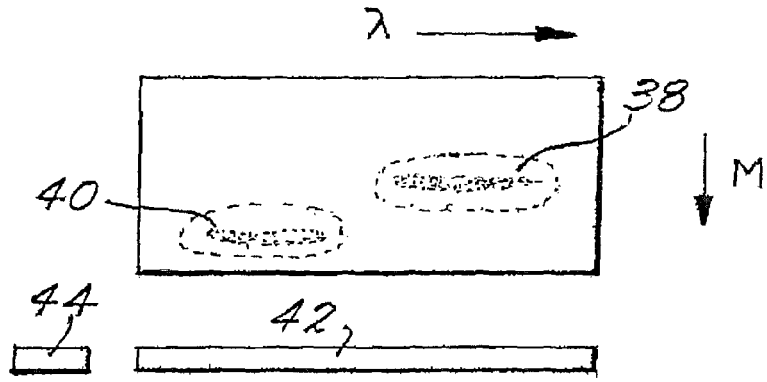
FIG. 3 is a view similar to FIG. 2 showing the image at a time t+$\Delta$t.

Referring additionally now to FIGS. 2 and 3, an image produced by moving analytes or analyte bands can be recorded by the photo-detecting surface of CCD 32 (FIG. 1) at times t (FIG. 2) and t+Δt (FIG. 3). Although the term analyte band is used herein, it is to be understood that an analyte band can include a single analyte, such as a single cell. The photo-detecting surface 36 can be part of the two dimensional detector array 34 shown in FIG. 1. Photo-detecting surface 36 can include a spectral axis as indicated by arrow λ on the figure, and a spatial axis along which the analyte bands move, as indicated by arrow M, in FIGS. 2 and 3. As further seen in FIG. 2, an image created by the light signals emitted by excited markers can produce, for example, two bands 38 and 40 on photo-detecting surface 36, for example, substantially in the red and blue regions of the spectrum, respectively. Each band can correspond to a marker used to label, for example, a predetermined type of analyte. The bands can be spectrally distributed along the spectral axis by transmission grating 28 as shown in FIG. 1. At time t, as shown in FIG. 2, the charges produced on surface 36 can present two respective peaks 46 and 48 on intensity profile 45. These peaks can correspond to bands 38 and 40, respectively. As seen in FIG. 3, at time t+Δt, both bands 38 and 40 can have moved downward along the direction of migration M on the photo-detecting surface 36. Serial register 42 of the CCD 32 (FIG. 1) collects the charges accumulated for each analyte band during its integration time. All signals received from the detector can be converted from analog to digital, and conveyed to a serial port for transmission to a multipurpose computer for storage and/or for further processing and analysis. The analog output can alternatively or additionally be sent directly to an output device for display or printing, or used for other purposes.

According to various embodiments, for example, as shown in the embodiment above, collection of the image can be performed using time delay integration (TDI). In the CCD, the photogenerated charge in the photoactive elements or pixels can be transferred toward the serial register 42 one row at a time. The charge information in the serial row can be read by using a corresponding single on-chip amplifier or readout register 44 of the CCD. By way of example, for a 256×256 element CCD, each time a single imaging area (one row) is transferred to the serial register 42, 256 readouts of the thus transferred area are performed, each readout corresponding to a different spectral element or pixel in the row. The above process continues until all 256 pixels in all 256 rows have been read.

Under a normal read-out approach, the motion of the images on the detector array 34 produces a blur. In TDI, according to various embodiments, the shutter can be eliminated. The shifting of rows of the CCD can be synchronized to the migration of the band of analyte in the channel. Thus, as an analyte band enters the excitation zone of the LED (detection zone 14), the light signals emitted therefrom can be collected and can illuminate the first row of the CCD, and the corresponding charge information can be read using the amplifier or readout register 44 of the CCD. The band takes a period of time, Δtp, to migrate in the channel so that its corresponding image migrates to the next row of the CCD, one row closer to the serial register. After this time period, the charge on the CCD can be shifted one row closer to the serial register, such that the fluorescence from the analyte corresponds to the same charge information on the CCD. Therefore, distinct from the physical rows of the CCD, there exists in TDI according to various embodiments a continuously moving row of accumulating photogenerated charge. An example of TDI in a capillary electrophoresis system using laser-induced fluorescence is disclosed in U.S. Pat. No. 5,141,609 to Sweedler et al., and in J. F. Sweedler et al., *Fluorescence Detection in Capillary Zone Electrophoresis Using a Charge-Coupled Device with Time Delayed Integration*, Anal. Chem. 63, 496-502 (1991), the contents of both of which are incorporated herein in their entireties by reference.

According to various embodiments, the effective integration time for a given analyte band can vary from application to application. The effective integration time of a given analyte band can correspond to a time where the portion of the wavelengths of the light signals in the analyte band being integrated moves across two pixels on the detector array, or to the entire time the portion of the wavelengths of the light signals in the analyte band being integrated is in the detection zone, or to any time therebetween. In addition, the portion of the wavelengths of the light signals in the analyte band being integrated can, according to various embodiments, include (1) a range of wavelengths about a peak intensity of the light signals; (2) a range of wavelengths including all wavelengths of the light signals; or (3) a range of wavelengths anywhere between (1) and (2) above. By way of example, the integration time can include a time it would take for the detector to integrate a range of wavelengths of the analyte band corresponding to a full width of an intensity curve of the light signals in the analyte band at half of the peak or maximum intensity of the intensity curve, or "full width at half max" of the intensity curve. The portion of the wavelengths of the light signals in the analyte band being integrated can depend on the number of different colors being integrated, and on how well the colors are separated from one another in the emission spectra. As a general rule, the better separated the colors in the emission spectra, the wider the portion of the wavelengths of the light signals, and, hence, the longer the effective integration time.

According to various embodiments, the use of TDI in collecting data points addresses the problem of lowered irradiance when using irradiation sources emitting non-coherent light, such as LEDs. The irradiance, that is, photons emitted per millimeters squared, can be typically about a thousand times lower in LEDs when compared with the irradiance of lasers. According to various embodiments, TDI addresses the problem of lowered irradiance by allowing a longer period of time for the integration of signals from excited markers. According to various embodiments, a broad detection zone can be used for TDI. In a non-TDI detection system, the detection zone can be typically about one tenth of a millimeter squared. When using TDI according to various embodiments, the detection zone for one channel can be one hundred times larger, that is, about one millimeter squared, allowing a relatively larger number of markers to be excited and a larger number of data points to be integrated into a detector. The various embodiments described herein can be equally applicable in instances where a plurality of channels are present, the detection zones of each of the respective channels being adapted to be irradiated by one or more irradiation sources emitting light.

For the purpose of accumulating charges to effect TDI, instead of shifting the charges on the CCD as a function of the migration of the analyte bands, according to various embodiments, the CCD itself and/or the image itself, that is, the light signals from the detection zone, can be moved as a function of migration of the analyte bands. The result of such movement of the CCD and/or image can be the tracking of each analyte band by a continuously moving row of accumulating photo-generated charge on the CCD during the effective integration time of the analyte band. By way of example, to accomplish the desired result mentioned above, appropriate motors, gearing, belt drives, control units and power supplies can be used. For example, a linear actuator can be used to translate the re-imaging optical system 30 and/or the CCD itself to minimize blurring. This can make the image stationary on the CCD throughout the integration time.

According to various embodiments, the CCD can be a frame transfer CCD. A frame transfer CCD has a parallel register that can include two CCD registers arranged in tandem. The CCD register, or storage array adjacent to the serial register, can be covered with an opaque mask and can provide temporary storage for charges during readout. The other CCD register, or image array, identical in capacity to the storage array, can be used for imaging. After the image array is exposed to light, the resulting charges can be rapidly shifted in the parallel register up to the storage array for subsequent readout. This shift operation typically takes a millisecond. While the masked storage array is being read, the image array can integrate charge from the next image. See *Charge-Coupled Devices for Quantitative Electronic Imaging*, Photometrics Ltd. (1992), the content of which is incorporated herein in its entirety by reference.

To effect TDI, according to various embodiments, the modulating optics as defined herein can be moved relative to a channel-defining member. For example, over a given detection zone, the modulating optics can be moved along the detection zone at substantially the same speed as the analyte for detection moves along the detection zone in the channel-defining member. In this manner, the marker of a component of the analyte band can be repeatedly imaged on the same portion of the detector, for example, a CCD, over the integration time. Alternately, the channel-defining member can be moved at the same speed but in an opposite direction from the movement of the analyte along the channel-defining member. Movement of the channel-defining member opposite the movement of the analyte to be detected can give the appearance of the analyte remaining stationary. Movement of the channel-defining member opposite the direction of movement of the analyte, in combination with movement of the modulating optics opposite the direction of movement of the analyte to be detected, can be used in combination in order to accumulate data on all analytes in the channel-defining member.

Referring now to FIGS. 4, 5a, and 5b, and according to various embodiments, instead of one irradiation source, a plurality of irradiation sources can be provided to excite marker compounds in a sample. In the embodiment shown in FIGS. 4, 5a, and 5b, the irradiation sources can include four LEDs 50, 52, 54 and 56. The LEDs can be positioned so as to irradiate channel-defining member 58, which can define two channels in the form of, for example, two capillary tubes, as shown in FIG. 5b. Each LED can emit non-coherent light in a predetermined range of wavelengths. For example, LED 50 and LED 52 can emit substantially blue light, LED 54 can emit substantially green light, and LED 56 can emit substantially yellow light. As the above example shows, multiple LEDs can be used to increase the available light. For example, if LEDs 50 and 52 emit blue light, they can be used simultaneously, either continuously or in a pulsed fashion, in this way increasing the amount of available blue light to obtain a proportional response in the associated markers. Although each type of marker used can ideally be excited by a different wavelength, LEDs of the optimum wavelength and power level for excitation of a given marker may not be available for each given application. Thus, different markers can be excited by the same LED, according to various embodiments.

According to various embodiments, the modulating optics according depicted in FIGS. 4, 5a, and 5b, can be comparable to the modulating optics in the embodiment shown in FIG. 1, with like components having been labeled with like reference numerals. Thus, for each irradiation source, a conditioning filter 18 and a focusing optical system 19 are provided, it being understood that the respective conditioning filters and focusing system for the respective irradiation sources are not, however, necessarily identical merely by virtue of the fact that they have been labeled with like reference numerals. As previously noted with respect to FIG. 1, the function of each conditioning filter 18 can be to let through only light in the wavelength range of excitation light for one or more of the markers. The conditioning filters 18 each can substantially block predetermined ranges of wavelengths of light emitted by the corresponding LED. The predetermined ranges correspond to wavelengths of light that can overlap with the emission spectra of the markers being excited by the corresponding LED. Each focusing optical system 19 can focus the conditioned light from the conditioning filter onto the detection zone 14. As shown, for example, in FIGS. 4, 5a, and 5b, the detection zone 14 can correspond to a respective detection zone for each of the shown capillary tubes. Excited markers in detection zone 14 can emit light signals in the form of emitted light 22. The light from the detection zone can include the emitted light 22, and, in addition, a portion of the conditioned light 20 passing through the detection zone.

According to various embodiments, the light 20/22 from the detection zone can be collimated by collimating optical system 24, as shown, for example, in FIG. 5a. The collimated light can be passed through a corresponding bandpass filter 51 on filter wheel 60 as shown in broken lines in FIGS. 5a and 5b. It can be noted that the bandpass filters 51, 53, 55, 57, and FD, in FIGS. 5a and 5b have been shown in broken lines because, in those figures, the depiction of the filter wheel 60 is not cross-sectional, but rather represents plan views thereof.

Referring to FIG. 4, the filter wheel 60 is shown in more detail, and includes a plurality of bandpass filters 51, 53, 55, 57, and FD. Each of the bandpass filters can be adapted to let through, substantially exclusively, predetermined wavelengths of light from the detection zone corresponding to a portion of the wavelengths of the light signals emitted by an associated marker. According to various embodiments, there can be a bandpass filter provided for each associated marker. The portion of the wavelengths of the light signals allowed through a respective bandpass filter can include all of the light signals emitted by an associated marker, or it can include a range of wavelengths about the peak intensity of the light signals emitted by the associated marker. For example, the range of wavelengths about the peak intensity of emitted light signals can be between about 5% and about 20% of wavelengths on each side of the peak intensity for a given marker, or it can include the range of wavelengths at about half of the peak intensity, full width at half max. For example, as shown in FIGS. 4, 5*a*, and 5*b*, bandpass filter 51 can be adapted to filter therethrough light signals emitted by given markers responsive to LED 50. In FIGS. 5*a* and 5*b*, the apparatus can be depicted in a mode where LED 50 can irradiate the detection zone 14. However, any of the shown LEDs 50, 52, 54, and 56, can be selectively used to irradiate the detection zone 14, or the detection zone 14 can be irradiated by more than one LED. The filter wheel 60 can be actuated by a filter wheel mechanism 62, as shown in FIG. 5*a*. The filter wheel mechanism 62 can control the filter wheel to selectively position, in the path of the collimated light, the bandpass filter corresponding to the marker excited by the active LED, that is, by the LED being used to irradiate the detection zone. Filter wheel mechanism 62 can be controlled by a microprocessor or other similar device (not shown) as known to those skilled in the art. The filtered light can be focused by a re-imaging optical system 30 onto an array 34 of solid-state detectors, or detector array 34, for example, the photo-detecting surface of the parallel register of a charge-coupled device, for example, CCD 32. According to various embodiments, a single LED can be used to excite all markers, or multiple LEDs can be used with one LED exciting each respective marker, or multiple LEDs can be used to excite a marker, or combinations thereof. The selection and number of bandpass filters for use can be a function of the markers themselves, the number of LEDs, or other factors as knows to those skilled in the art.

According to various embodiments, and as shown in FIG. 4, the filter wheel can include a filter FD thereon, adapted to let through only light signals generated by a fifth marker. Four markers can be used to label the moving analytes where the analytes are DNA fragments, each marker corresponding to a given one of the bases in a DNA chain, that is, purines A (adenine) and G (guanine), and pyrimidines C (cytosine) and T (thymine). According to various embodiments, a fifth marker can, for example, be used for fragment analysis of the analytes. The fifth marker can be any marker, such as a dye marker, for doing fragment analysis as known to those skilled in the art. It is to be noted that, according to various embodiments, the number of markers that can be used are not limited to four or five as stated in the above example, but are rather limited only by the number of dyes available on the market and responsive to the irradiation source or sources being used based on application needs. Fragment analysis can be accomplished using, for example, the GENESCAN® Analysis software produced by Applied Biosystems, Inc., Foster City, Calif. The GENESCAN® Analysis software calculates the size of the unknown analytes by generating a calibration or sizing curve based upon the migration times of the analytes in a standard that have been labeled with a marker. The unknown analytes can be mapped onto the curve and converted from migration times to sizes. In the case of the embodiment shown in FIG. 4, the fifth marker filter FD on filter wheel 60 can let through light signals corresponding to markers used to label analytes in the standard. These markers can be excitable by at least one of the irradiation sources 50, 52, 54, and 56, appropriately mounted to allow fragment analysis.

FIGS. 6*a* through 6*e* depict images on the detector array 34 of CCD 32 shown in the embodiment of FIGS. 4, 5*a*, and 5*b*, wherein the images can be produced by moving analyte bands. Exemplary images are shown for exemplary markers that can be used to label the analytes, and that can be responsive to excitation by a given one of the irradiation sources 50, 52, 54, and 56. Each frame of photo-detecting surface 36 shown in FIGS. 6*a* through 6*e* depicts two lanes of analyte bands, each lane corresponding to one of the two capillaries of channel-defining member 58. The bands move along the direction of migration M. The bands are shown in each of FIGS. 6*a* through 6*e* as being limited in the spectral direction because the light recovered from the markers has been filtered through a corresponding bandpass filter 51, 53, 55, 57, or FD. At the right of each frame is an intensity profile 45 corresponding to charges on the right lane of photo-detecting surface 36, which corresponds to a capillary of channel-defining member 58.

According to various embodiments, the intensity profiles can be aligned and combined according to known methods. The intensity profiles can be multicomponented in order to account for any spectral overlap. As described with regard to the embodiment of FIG. 1, the serial register of the CCD 32 in the embodiments depicted in FIGS. 4, 5*a*, and 5*b*, collects the charges accumulated for each analyte band during its integration time. All signals received from the detector can be converted from analog to digital and conveyed to a serial port for transmission to a multipurpose computer for storage, further processing, and analysis. Alternatively or additionally, the analog output can be sent directly to an output device for display or printing. By way of example, a multipurpose computer can be used to perform the multicomponenting process. Multicomponenting is a process that is known to those skilled in the art, and can involve a spectral calibration within a multicomponenting software program. The spectral calibration can be obtained through a predetermined signature matrix corresponding to each marker. Each signature matrix can provide a signature snapshot of the intensity of light signals from a given marker as a function of the wavelengths of those light signals. By virtue of the signature matrices, a combination of intensity curves for a given wavelength band emitted from the detection zone can be broken down into its components corresponding to light signals emitted by individual ones of the markers. In this way, a relatively accurate assessment of the light signals corresponding to respective ones of the markers can be made for the detection process.

According to various embodiments, the apparatus as shown, for example, in FIGS. 4, 5*a*, and 5*b*, can irradiate detection zone 14 by irradiating each respective one of the irradiation sources 50, 52, 54, and 56, in sequence. The filter wheel can be adjusted to dispose a bandpass filter 51, 53, 55, 57, or FD, corresponding to the marker being used before collimating optical system 24. The detection zone can be irradiated for the duration of the integration time, during which the analyte bands move across the detection zone. During the integration time, the charges generated by the light signals from the markers to be detected can be moved along a parallel register in the direction of migration. The charges can be accumulated in the detector or CCD 32 before they are read. Thereafter, the process can be repeated until all of the irradiation sources have irradiated the detection zone, and until all filters, including filter FD, have been positioned before the collimating lens to filter the light therefrom. Detector 32 can be a frame transfer CCD, wherein each frame of the CCD upon which charges have been accumulated can be transferred to a storage array, making the image array available for the next series of charge accumulations produced by the next respective one of the irradiation sources being used.

The above process can be repeated in cycles as many times as necessary in order to obtain sufficient data regarding each analyte being detected. Fewer cycles can result in an increase in signal, because fewer cycles mean longer integration times, and therefore increased readout signals over the noise typically associated with a CCD. On the other hand, increasing the number of cycles can improve the dynamic range of the system. The dynamic range of the system is defined as the largest peak signal that can be read by a given CCD (or "full well capacity") over the smallest peak that can be read by the CCD just above the noise level. A CCD typically has a given full well capacity. If a peak signal is above the full well capacity of a CCD, it will be off the scale of the CCD. Short integration times allow peak signals to be generally attenuated so as to reduce the possibility of saturating the CCD with off-scale signals, that is, with signals that go beyond the CCDs full well capacity. By using more cycles, analyte concentrations can be increased while still allowing the CCD to reliably detect signal levels without saturation. According to various embodiments, there is a trade-off between using fewer cycles at a longer integration time such as, for example, 5 seconds, and using more cycles at a shorter integration time such as, for example, 1 second. Longer integration times are useful where the noise level is relatively high and the sensitivity of the system needs to be increased because of the noise level. In systems where the noise level is relatively low, shorter integration times allow multiple reads of signals from the same marker, and the read signals can be multicomponented, allowing the detection of brighter peaks without going off the scale of the CCD.

By way of example, a frame transfer CCD can collect light signals corresponding to a blue marker during integration time t while an LED exciting primarily the blue marker irradiates the detection zone. Thereafter, the entire CCD is read out. A filter wheel can be moved to position a bandpass filter associated with a green marker before a collimating optical system, and an LED exciting primarily the green marker can irradiate the detection zone. The CCD can collect the light signals corresponding to the green marker during integration time t. The entire CCD is then read out. The filter wheel can be moved to position a bandpass filter associated with a yellow marker before a collimating optical system, and an LED exciting primarily the yellow marker can irradiate the detection zone. The CCD then collects the light signals corresponding to the yellow marker during integration time t, and the entire CCD is thereafter read out. The above process can be repeated for all five markers, for example, as shown in FIGS. 4, 5a, and 5b. The process can be repeated a number of times equal to the number of markers. According to various embodiments, one or both of the LED and bandpass filter can be changed between CCD readouts. As suggested in the above example, the image of the analyte band can take about five times the integration time to travel from the top of the frame transfer CCD to the bottom thereof, that is, to the readout register. Each readout of the CCD can correspond to one marker. All of the readouts can be aligned and combined in a known manner for multicomponenting.

Figure 6F:
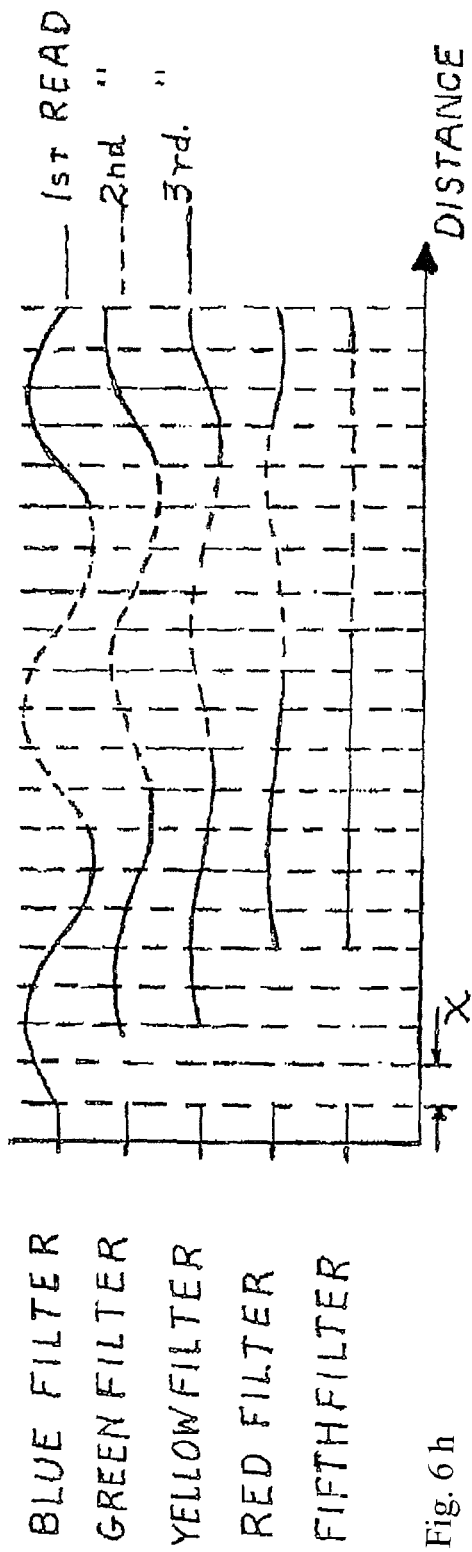
FIG. 6f is a schematic representation of an electropherogram showing fluorescence intensity curves for each filter of the filter wheel in FIG. 4 during three signal readings by the detector.
Figure 6G:
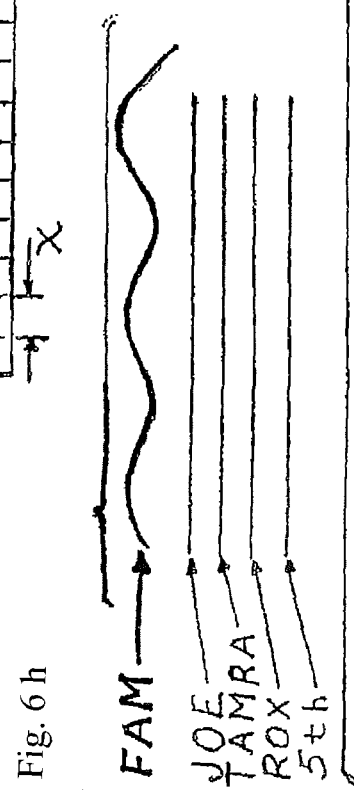
FIG. 6g is a schematic representation of the intensity curves of FIG. 6f in aligned format for multicomponenting.
Figure 6H:
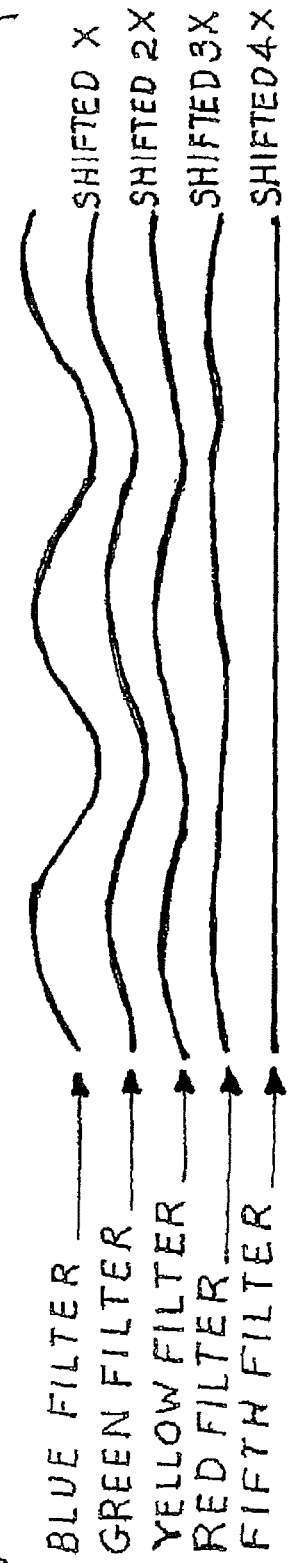
FIG. 6h is a schematic representation of multicomponented intensity curves for five different kinds of markers that can be used in the system of FIG. 4 based on the readings shown in FIG. 6f.

An example of multicomponenting is shown in FIGS. 6f through 6h. For purposes of FIGS. 6f through 6h, the filters 51, 53, 55, 57, and FD, are presumed to pass wavelengths of light in the blue, green, yellow, red and "fifth" portions of the spectrum, respectively. The "fifth" portion can, for example, be in the orange range of the spectrum. FIG. 6f is a schematic representation of an electropherogram showing fluorescence intensity curves during three readings of the signals by detector 32, wherein each curve corresponds to light passed through a respective filter of the filter wheel in FIG. 4. The intensity curves correspond to a reading of light signals emitted from an analyte labeled with a marker, for example, FAM, a dye marker that emits light signals mostly in blue. The first portion of each curve, drawn in solid lines, corresponds to a reading from the respective blue filter, green filter, yellow filter, red filter, or fifth filter of FIG. 4 during a first integration time t. The second portion of each curve, drawn in broken lines, corresponds to a reading from the respective filter during a second integration time t. The third portion of each curve, drawn in solid lines, corresponds to a reading from the respective filter during a third integration time t. In FIG. 6f, the horizontal axis corresponds to distance traveled by the analyte, and the vertical axis corresponds, for each filter, to the fluorescence intensity of light emerging from that filter. Thus, the first set of curves in solid lines represents intensity curves for light passing through each filter during a first cycle of the filter wheel 60. The second set of curves in broken lines represents intensity curves for light passing through each filter during a second cycle of the filter wheel 60. The third set of curves in solid lines represents intensity curves for light passing through each filter during a third cycle of the filter wheel 60. As seen in FIG. 6f, the light from the blue filter exhibits the most intensity during each cycle, the intensity decreasing as light is collected from the green filter, the yellow filter, the red filter and the fifth filter, respectively. As seen in the instant example, therefore, spectral overlap causes FAM to emit mostly in blue, some in green, less in yellow, etc. As filter wheel 60 is rotated within each cycle, to place a subsequent filter in the path of fluorescence from the detection zone 14, the analyte moves a distance x as marked on FIG. 6f.

FIG. 6g is a schematic representation of the intensity curves of FIG. 6f in an aligned format for multicomponenting. Each intensity curve other than the one corresponding to blue light can be shifted by a multiple of x, x being a function of the filter to be aligned with the intensity curve corresponding to blue light. After being aligned, the intensity curves are combined and multicomponented, yielding the intensity curve for FAM shown in FIG. 6h. To the extent that only FAM is being detected in the example of FIGS. 6f through 6h, the intensity curves for marker dyes JOE, TAMRA, ROX, and the fifth dye, are shown as flat in FIG. 6h.

Figure 6I:
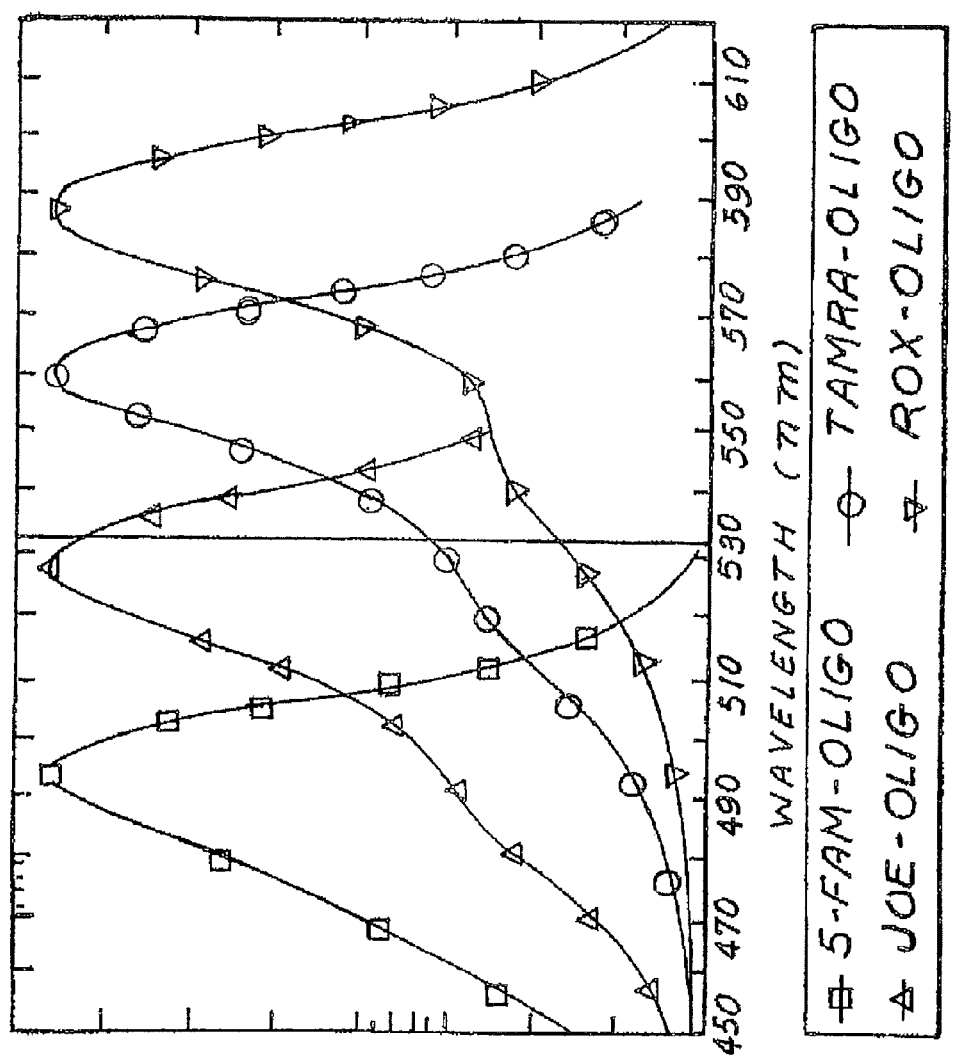
FIG. 6i is a graph of excitation efficiency versus wavelength for four exemplary markers.
Figure 6J:
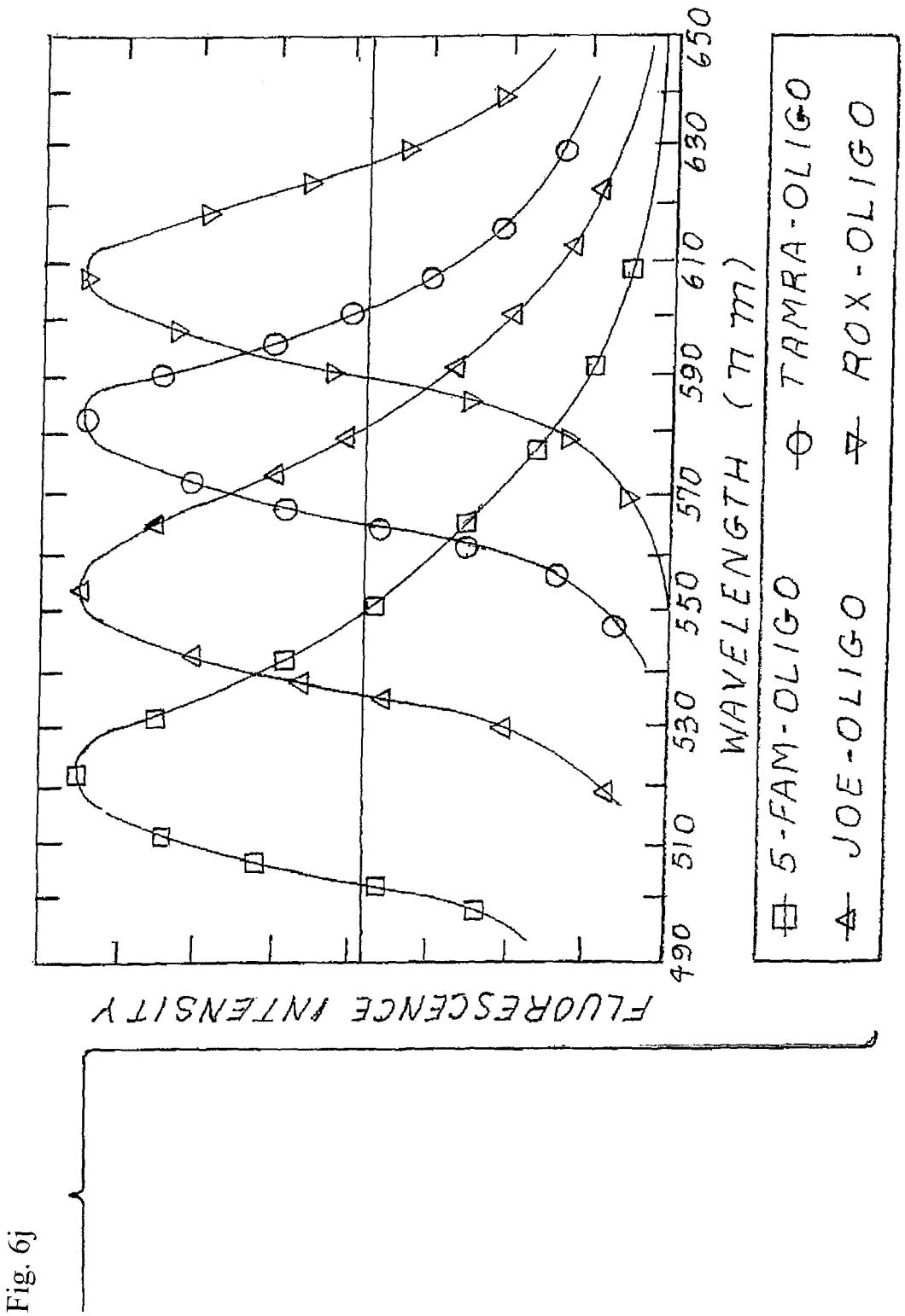
FIG. 6j is a graph of fluorescence intensity versus wavelength for the exemplary markers of FIG. 6i.

FIGS. 6i and 6j demonstrate representative excitation efficiency curves and fluorescence intensity curves, respectively, plotted versus wavelength for four different dye markers that can be used in oligosynthesis, namely, 5-FAM, JOE, TAMRA, and ROX. These dye markers are exemplary of those that can be used in various embodiments where a plurality of dye markers are to be used, such as with systems shown in FIGS. 4, 5a, 5b, and 7.

In FIG. 6i, the x-axis corresponds to wavelengths, expressed in nanometers (nm), emitted by an irradiation source. The y-axis corresponds to the percentage of excitation efficiency. As shown in FIG. 6i, 5-FAM has a maximum absorbance, corresponding to its peak percent excitation efficiency, at about 490 nm. When maximum absorbance of a dye marker occurs at a given wavelength, it indicates that the dye marker fluoresces at its peak fluorescence intensity when it is irradiated at that given wavelength. As further shown in FIG. 6i, JOE has a maximum absorbance at about 526 nm, TAMRA has a maximum absorbance at about 560 nm, and ROX has a maximum absorbance at about 588 nm. FIG. 6i also shows that, when a dye marker, such as 5-FAM, is irradiated at its maximum absorbance wavelength, other dye markers, such as, for example, JOE, TAMRA, and ROX, do exhibit some absorbance, although to a lesser extent than 5-FAM. Any irradiation source, for example, an LED, can be used to emit the wavelengths indicated on the x-axis.

In FIG. 6j, the x-axis corresponds to wavelengths of fluorescent light, expressed in nm, emitted by excited dye markers. The y-axis corresponds to the percentage of fluorescence intensity. As seen in FIG. 6j, 5-FAM has a peak fluorescence intensity at about 522 nm, JOE has a peak fluorescence intensity at about 554 nm, TAMRA has a peak fluorescence intensity at about 582 nm, and ROX has a peak fluorescence at about 608 nm. The wavelengths on the x-axis are those that can be emitted by the four mentioned dye markers. FIG. 6*j* shows that where a dye marker, such as TAMRA, fluoresces at its peak fluorescence intensity, other dye makers, such as 5-FAM, JOE, and ROX, also fluoresce, although at lesser fluorescence intensities than TAMRA.

When different light wavelength sources are used, each dye marker in the detection zone can be excited efficiently, and in a way that allows detection by its unique spectral signature. When two dye markers exhibit fluorescence intensity peaks that are close together, for example, when the difference between the fluorescence intensity peaks of the two dye markers is less than about 30 nm, there can be a high level of overlap of the light emitted by the two dye markers. A high level of overlap can make it difficult to distinguish between the light emitted by the two dye markers, and therefore can make it difficult to determine the relative amounts of the two dye markers. Typically, there is overlap present in the excitation and emission wavelengths of the different dye markers, as suggested, for example, in FIGS. 6*i* and 6*j*. However, the overlap can be minimized by selecting dye markers that present easily distinguishable fluorescence intensity peaks, such as those shown in FIG. 6*j*. According to various embodiments, it is possible to first start with an irradiation source emitting radiation within a given range of wavelengths, and to investigate each such irradiation source to see how well it excites available dye markers. Graphs such as those shown in FIGS. 6*i* and 6*j* can be used in this context. For example, where excitation efficiency curves of various dye markers are plotted as shown in FIG. 6*i*, an irradiation source, such as an LED emitting light in a given range of wavelengths, can be predicted to excite given ones of the dye markers based on their excitation efficiencies. Using a fluorescence intensity graph as shown in FIG. 6*j*, the amount of overlap between intensity peaks of the different markers can be determined. Using this information, a set of dye markers best suited for a particular application can be chosen. Once the dye makers are chosen, the filters corresponding thereto can be chosen, for example, the filters shown on the filter wheel of FIG. 4 described above, and on the filter wheel of FIG. 7 described below. The best set of markers can exhibit the desired minimum amount of overlap at the emitted wavelengths that are to be detected.

Because each marker can have a different excitation curve, the fluorescence output of a marker can be dramatically increased by the use of an LED that is well matched to the excitation wavelength of the marker. Matching the light source and marker can increase emission from the marker of interest, while minimizing undesired light, for example, background light from the system and emissions from other markers, resulting in better quality data. For example, if a blue/green LED having an emission wavelength of about 503 nm is used for the marker designated FAM, the excitation of FAM can be high, about 80%, and the excitation for another marker, for example, ROX, can be low, for example, about 6%. Similarly, a yellow LED with an emission wavelength of about 592 nm will not excite FAM, but can excite ROX in an amount of about 90%.

Figure 7:
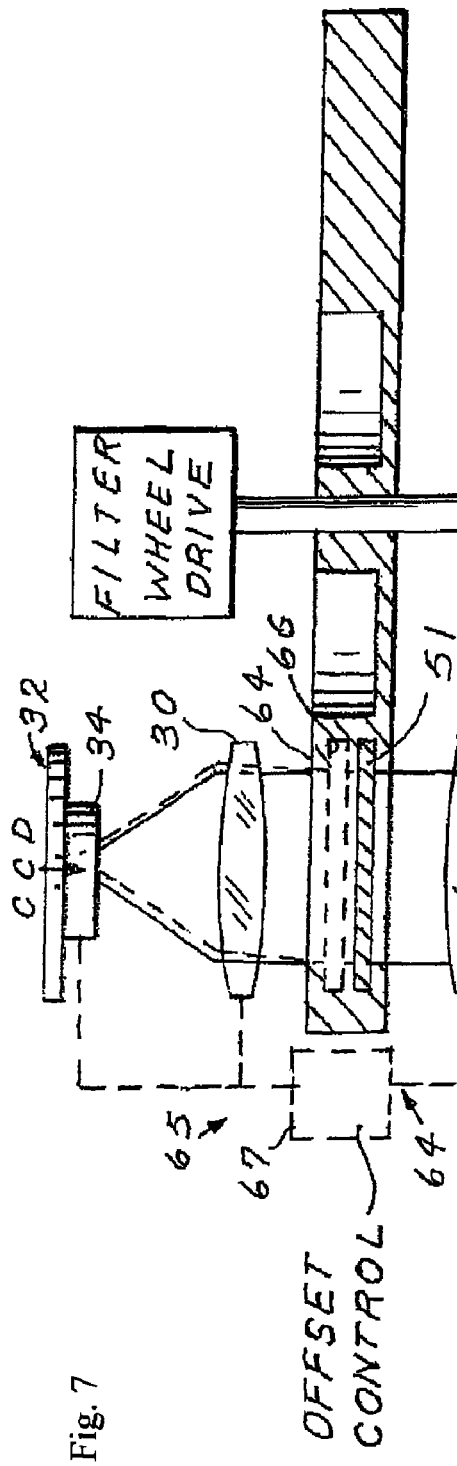
FIG. 7 is a top-plan, partially cross-sectional view, of an electrophoresis arrangement for the sequential use of multiple color irradiation sources along with filters on a filter wheel and along with an offset system, according to various embodiments.

Another embodiment of an apparatus is depicted in FIG. 7. As in the embodiments shown in FIGS. 4, 5*a*, and 5*b*, a number of irradiation sources can be used to sequentially irradiate a detection zone. The generated light signals having wavelengths in differing frequency ranges can correspond to charges spatially offset on the same array of the detector, wherein the offset is a function of the bandpass filter used in connection with the markers emitting the light signals. Reading of the accumulated charges on the detector array during time delay integration (TDI) can be continuous rather than a frame-by-frame reading.

As shown in FIG. 7, the irradiation sources, together with associated optics such as the conditioning filter 18 and the optical system for focusing 19, can be provided on an irradiation source wheel 61. Components of the apparatus of FIG. 7 that are similar to those in FIG. 1 have been labeled with the same reference numerals, such as conditioning filter 18, focusing optical system 19, collimating optical component or system 24, and re-imaging optical component or system 30. An irradiation wheel 61 can be rotatable to selectively position each respective one of the irradiation sources and associated optics to irradiate a detection zone 14. Any number of irradiation sources, for example, four irradiation sources 50, 52, 54, and 56, as shown, for example, in FIGS. 4, 5*a*, and 5*b*, can be provided. A filter wheel 61' can be provided, similar to filter wheel 60 in FIGS. 4, 5*a*, and 5*b*. The rotation of both wheels 61 and 61' can be effected by the provision of a filter wheel drive 62 similar to the filter wheel drive of FIGS. 4, 5*a*, and 5*b*, described above. According to various embodiments, the two wheels 61 and 61' can be coupled to one another and to the filter wheel drive 62 by way of a rotatable shaft 63. According to various embodiments, a plurality of irradiation sources can be provided that are not on an irradiation wheel. According to various embodiments, the two wheels 61 and 61' can be actuated independently by their own respective wheel drives, and are not coupled to one another by a shaft.

As shown in FIG. 7, the apparatus can be provided with an offset system 64. Offset system 64 can either be disposed on the filter wheel 61' in association with a corresponding bandpass filter, or can be coupled to at least one of a detector 32, one or more components of the modulating optics system, and the detection zone 14. The offset system 64 can spatially offset the light signals impinging upon the array 34 of the detector 32 by a predetermined amount as a function of the bandpass filter being used. The offset can be accomplished by an offset system 64 including a plurality of offset mechanisms 66 disposed on filter wheel 61', wherein the offset mechanism 66 is shown in broken lines in FIG. 7. Each offset mechanism 66 can be associated with a respective one of the bandpass filters to offset the filtered light therefrom. The offset mechanisms 66 can include one or more grating, mirror, prism, or any other device for offsetting light as known to those skilled in the art, or a combination thereof. One or more offset mechanism 66 can be distributed about the circumference of filter wheel 61' adjacent the corresponding bandpass filter, and between the bandpass filter and the detector 32, otherwise being identical to wheel 60 in FIG. 4. In the alternative, the offset can be accomplished by providing an offset system 64 including an offset control device 67, also shown in broken lines in FIG. 7. The offset control device 67 can be coupled to at least one of the detection zone 14, one or more component of the modulating optics system, and the detector array 34, in order to offset the light signals impinging upon the array 34 of the detector 32.

According to various embodiments, the offset system can move at least one of the detection zone 14, collimating optical system 24, re-imaging optical system 30, or detector array 34, by a predetermined amount in order to offset the light signals impinging upon the detector array 34. The offset system can include any suitable device for effecting a translational movement of at least one of the detection zone 14, collimating optical system 24, re-imaging optical system 30, or detector array 34, as known to those skilled in the art. Such devices can include, for example, solenoids, or motor driven linear actuators, for example, lead screws, rack- and pinion systems, cams, and the like. For example, a cam can be attached to drive shaft 63 to cause a predetermined translation of the re-imaging optical system 30 in a number of ways recognizable by those skilled in the art. The predetermined amount of translation can correspond in a one to one ratio with the amount by which the light signals impinging upon the detector array are sought to be offset. The range of wavelengths offset by the predetermined amount can be a function of the irradiation source, the markers, or other factors known to those skilled in the art.

The predetermined amount by which a given set of light signals corresponding to an irradiation source and its respective bandpass filter is to be offset can be readily determined by determining where on the detector array the charges produced by the given set of light signals corresponding to a specific bandpass filter should be situated with respect to the detector array itself, and with respect to sets of light signals in different wavelength frequency ranges corresponding to the other bandpass filters. Thus, where individual mechanisms 66 are used in conjunction with a corresponding bandpass filter to offset the light emerging therefrom, each mechanism 66 can be chosen according to the frequency range of wavelengths that the bandpass filter lets through. In the alternative, where offset control device 67 is used, the offset control can be programmed to offset at least one of the detection zone 14, one or more components of the modulating optics system, and the detector array 34, with respect to one another by the predetermined amount. The offsetting could, by way of example, be accomplished by moving the detection zone 14, the modulating optics, or the detector array 34, in a translational motion by the predetermined amount, causing the image created by the light signals to be correspondingly spatially offset. The embodiment shown in FIG. 7 can involve the use of a plurality of LEDs similar to those used in the embodiment of FIGS. 4, 5*a*, and 5*b*. The offset amount can be sufficient be prevent overlap of the images from each bandpass filter.

Offset system 64, including offset mechanisms 66, or, in the alternative, offset control device 67, is shown in broken lines in FIG. 7 in order to suggest that mechanisms 66 or offset control device 67 can be used as alternatives for the offset system 64. According to various embodiments, both alternatives, that is, mechanisms 66 and offset control device 67, can be used in conjunction with one another. The modulating optics can include at least one of conditioning filter 18, focusing optical system 19, collimating optical system 24, and re-imaging optical system 30, or any devices or systems known to achieve the functions associated with the components listed above as known to those skilled in the art.

According to various embodiments, the detection zone can include any suitable channel-defining member, for example, any number of capillaries, or any number of channels, in, for example, an etched plate. The channel-defining member can be a slab plate. According to various embodiments, the channel-defining member can assume any orientation according to application needs, for example, a horizontal orientation or a vertical orientation.

According to various embodiments, any suitable number of bandpass filters can be used, the number being determined at least in part by the markers being used. Any number of different irradiation sources, for example, LEDs, that can emit light in any number of wavelength ranges, can be used. The number of LEDs can be dependent, in part, on the amount of available space, the availability of LEDs corresponding to the excitation wavelength ranges of the marker(s), and/or the type of marker(s) that can be used.

As used herein, the term "optical system" can include a single lens, a lens system, a mirror system, or any other optical system capable of fulfilling the desired and stated functions, as readily recognizable by those skilled in the art.

In operation, the detection zone 14 in FIG. 7 is irradiated by a first one of the irradiation sources, for example, by LED 50, as depicted in FIG. 7. The light signals emitted by the markers excitable by the light from LED 50 can be, as previously described, filtered through a corresponding bandpass filter 51, and thereafter focused onto detector array 34 by a re-imaging optical system. Where offset system 64 includes mechanism 66, the filtered light from bandpass filter 51 is offset by a respective mechanism 66 by the predetermined amount corresponding to the range of wavelengths that the bandpass filter lets through, as described above. Each subsequent irradiation source and corresponding bandpass filter can be positioned to irradiate the detection zone and to filter the light therefrom through a rotation of the wheels 61 and 61' in conjunction with one another. As previously suggested, any suitable number of markers, bandpass filters, and LEDs can be used in the system.

In the embodiment of FIG. 7, charges can be accumulated for each respective irradiation source during the integration time of the analyte bands excitable by light from the respective irradiation source. The accumulation of charges can be effected, as previously described, by shifting the charges on the detector array, by moving relative to one another the detector array and light signals from the detection zone, by moving the modulating optics relative to the channel-defining member, or a combination thereof. After each integration time, the wheels 61 and 61' can be rotated to position the next irradiation source and corresponding bandpass filter in a functional position, that is, in a position for the irradiation source to irradiate the detection zone and for the bandpass filter to filter the light from the detection zone. The process can be repeated until one cycle is completed, that is, until all of the irradiation sources and filters have been used once. The cycle can be repeated as many times as necessary and/or desired on an application-by-application basis. To the extent that the exemplary embodiment of FIG. 7 includes an offset system for spatially offsetting light signals in differing frequency ranges, the exemplary embodiment can allow a continuous reading of accumulated charges by the detector, thereby making possible a continuous time delay integration of the light signals from the analytes into the detector array 34. Alternately, as shown in the exemplary embodiments of FIGS. 4, 5*a*, and 5*b*, the accumulated charges corresponding to each range of wavelengths of light signals can be read and discarded by the detector before charges for the next range of wavelengths are read.

Figure 8:
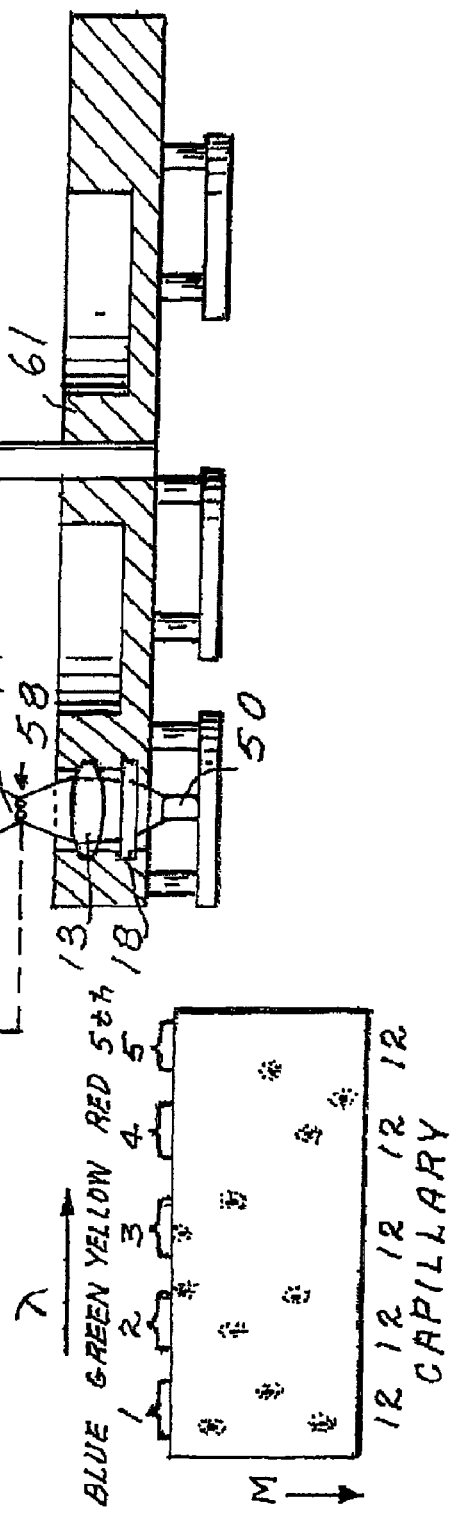
FIG. 8 is a schematic view of an image produced on the detector array of a detector using the arrangement of FIG. 7.
Figure 9:
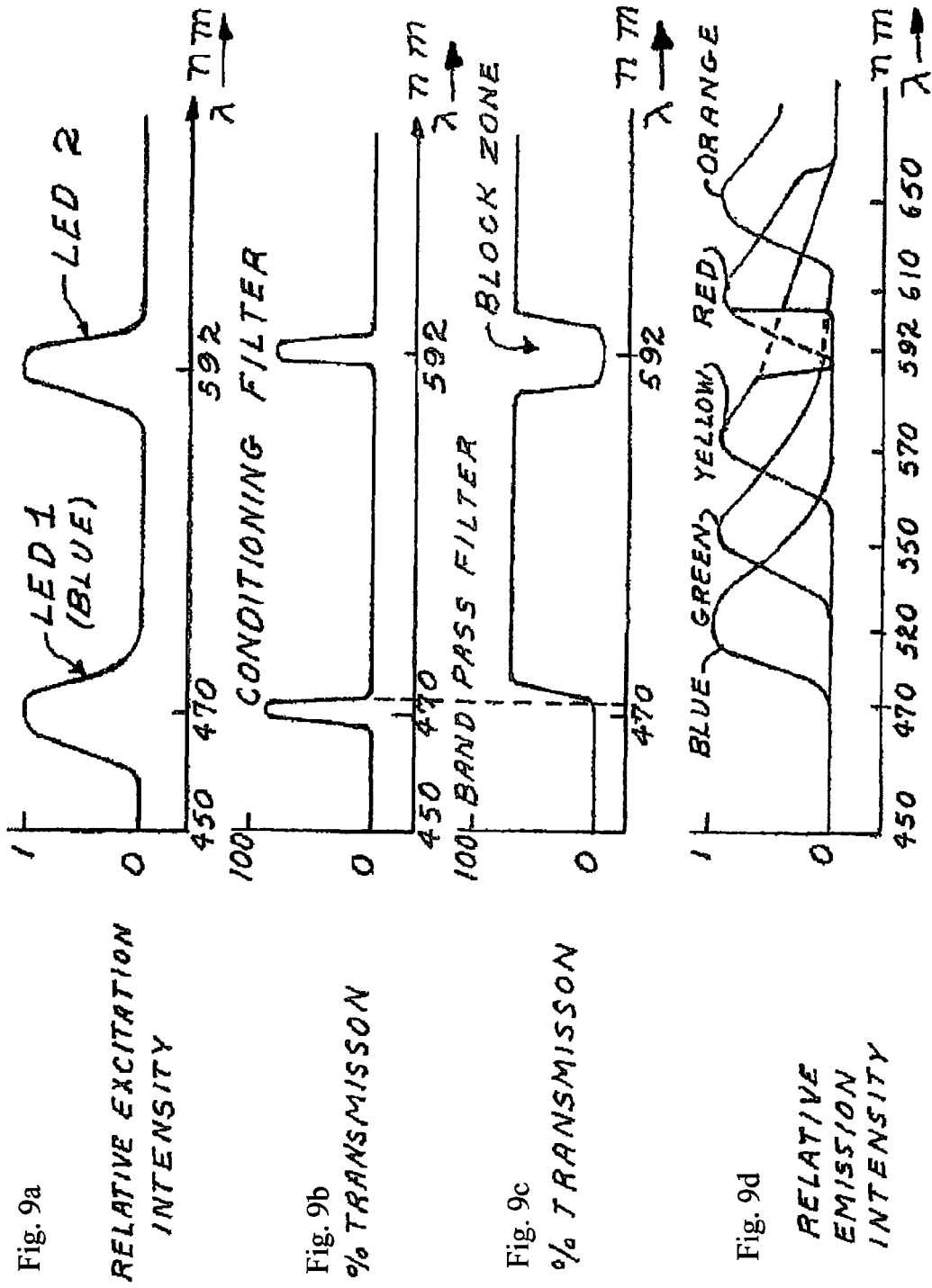

FIG. 8 depicts an exemplary image that can be produced on the array of detector (CCD) 32 by the moving analyte bands in each of the two capillaries 58 for each of the wavelength ranges. As depicted in the image, each range of wavelengths is assigned an arbitrary color, for example, "blue," "green," "yellow," "red," and "fifth." For each color, the column on the left corresponds to charges produced by light signals from one capillary, and the column on the right corresponds to charges produced by the second capillary. The array depicts charges generated by light signals across the color axis $\lambda$, offset with respect to one another by offset system 64 in the manner previously described. According to various embodiments, the number of wavelength ranges used can be dependent on the particular application, and can range from one to as many as the system supports. The X axis is referred to here as the "color axis" rather than the "spectral axis," because the colors, one for each bandpass filter, do not need to be arranged from shorter to longer wavelengths. According to various embodiments and as shown in FIG. 8, to the extent that charges from light signals of differing wavelengths can be produced on the same array of light signals so as to be spatially offset with respect to one another, those charges can be accumulated during the integration time and read by the detector on a continuous basis. This can eliminate the need to shut off the detector in order to allow a reading of charges in a given range of wavelengths on a frame-by-frame basis, and/or can eliminate the need for a frame transfer CCD. Further, a longer integration time and simpler data output can be achieved, and a cheaper CCD can be used.

According to various embodiments, the detection zone, including one or more channels, or a slab gel, can be irradiated with multiple color irradiation sources, for example, multiple color LEDs. The use of multiple color LEDs can greatly improve the absorption efficiency of some of the markers. According to various embodiments, an irradiation source can be conditioned to provide only a narrow wavelength range of light. A bandpass filter can be used to substantially block all of the unwanted excitation light from the irradiation source. As used herein, "irradiation source" can include one or more sources of irradiation. An example of the results, in the form of graphs demonstrating the effects of a conditioned irradiation source in combination with a bandpass filter, are illustrated in FIGS. 9a through 9d.

According to various embodiments and as depicted in FIGS. 9a through 9d, a detection zone of an apparatus can be irradiated by two irradiation sources simultaneously, although any number of irradiation sources can be used simultaneously according to various embodiments. A system such as the one shown in FIG. 1 can be used, replacing the single LED in FIG. 1 with a set of two or more LEDs. The associated optics can be altered according to the number of irradiation sources used.

According to various embodiments, a conditioning filter can be used for each set of LEDs. The conditioning filter can substantially block predetermined ranges of wavelengths of light emitted by the set of LEDs as previously described, each predetermined range corresponding to a respective LED, as demonstrated, for example, in FIG. 9a. FIG. 9a shows a graph of relative excitation intensity for each of two LEDs of a set of LEDs, versus wavelength expressed in nanometers. The graph of FIG. 9a depicts the two LEDs as being in the violet and orange portions of the spectrum, respectively. It is to be understood that various embodiments are not limited to the above two types of LEDs, but encompasses any number of LEDs emitting light in any range of frequencies according to application needs. As depicted in FIG. 9b, each predetermined range of wavelengths that passes through the conditioning filter corresponds to a subset of the wavelengths emitted by each respective LED depicted in the graph of FIG. 9a. The wavelengths that pass through the conditioning filter can be capable of exciting the markers responsive to each respective LED. FIG. 9b is a graph of percent transmission of light through the conditioning filter versus wavelength. As shown in FIG. 9b, the conditioning filter can substantially block all excitation light except for wavelengths around the respective LED emission maximum. For example, the conditioned light ranges can correspond to a wavelength range of from about 450 nm to about 490 nm, and to a second wavelength range of from about 580 nm to about 605 nm, corresponding to the first and second irradiation sources, respectively. The conditioning filter, and the predetermined ranges capable of passing therethrough, can be functions of the LED set being used.

According to various embodiments, the conditioning filter can include a single conditioning filter, or a series of conditioning filters, capable of filtering the light from the set of LEDs. The conditioned light can be focused onto the detection zone of an electrophoretic detection system, as previously described above. The light emitted by markers in the detection zone can be passed through a bandpass filter. The bandpass filter can allow, substantially exclusively, predetermined wavelengths of light from the detection zone to pass through, wherein the predetermined wavelengths of light correspond to a portion of the wavelengths of the light signals emitted by an associated set of markers. The light that passes through the bandpass filter can be filtered light. The bandpass filter can substantially block the excitation light from the LEDs which passes the detection zone. The portion of the wavelengths of the light signals that can pass through the bandpass filter can include all of the light signals, or a range of wavelengths about the peak intensity of light signals of each respective marker. For example, the range of wavelengths about the peak intensity of light signals can be between about 5% and about 20% of wavelengths on each side of the peak wavelength of a given marker, or it can include full width at half max. The collection of the predetermined wavelengths can be by dispersion, for example, as shown in FIG. 1, or by use of additional bandpass filters, as shown, for example, in FIG. 4.

According to various embodiments, a conditioning filter can be used between the irradiation source (light source) and the detection zone holding a sample solution. The beam emitted by the light source is also known as an excitation beam that can be filtered by an excitation filter at an excitation wavelength range. Comparably, a conditioning filter can be used between the detection zone holding the sample solution and a detector. The fluorescence or luminance emitted by the sample upon excitation is also known as an emission beam that can be filtered by an emission filter at an emission wavelength range.

According to various embodiments, a light source can be used to provide excitation beams to irradiate a sample solution containing one or more dyes. For example, two or more excitation beams having the same or different wavelength emissions can be used such that each excitation beam excites a different respective dye in the sample. The excitation beam can be aimed from the light source directly at the sample, through a wall of a sample container containing the sample, or can be conveyed by various optical systems to the sample. An optical system can include one or more of, for example, a mirror, a beam splitter, a fiber optic, a light guide, or combinations thereof.

According to various embodiments, one or more filters, for example, a bandpass filter, can be used with a light source to control the wavelength of an excitation beam. One or more filters can be used to control the wavelength of an emission beam emitted from an excited or other luminescent marker. One or more excitation filters can be associated with a light source to form the excitation beam. One or more filters can be located between the one or more light sources and a sample. One or more emission filters can be associated with an emission beam from an excited dye. One or more filters can be located between the sample and one or more emission beam detectors.

According to various embodiments, one or more filters, for example, a bandpass filter, can be used with a light source to control the wavelength of an excitation beam. One or more filters can be used to control the wavelength of an emission beam emitted from an excited or other luminescent marker. One or more excitation filters can be associated with one or more light sources to form at least one-excitation beam. One or more filters can be located between the one or more light sources and a sample. According to various embodiments, one or more emission filters can be associated with an emission beam from an excited dye. One or more filters can be located between the sample and one or more emission beam detectors.

According to various embodiments, a filter can be used that is a single bandpass filter or a multiple bandpass filter. As used herein, a bandpass filter and a passband filter are used interchangeably. A multiple passband filter can be, for example, a multiple-notch filter or a multi-Rugate filter. A multiple passband filter can be used with an incoherent light source, for example, a halogen lamp, a white light source, and/or one or more LEDs or OLEDs emitting light at different wavelengths. A multiple passband filter can be used with a multiple laser-based light source emitting light at different wavelengths. Examples of manufacturing and use of Rugate filters and Rugate beam splitters can be found in, for example, U.S. Pat. No. 6,256,148 to Gasworth which is incorporated herein by reference in its entirety.

According to various embodiments, a multiple passband filter can be used with a dichroic beam splitter, a 50/50 beam splitter, a dichroic beam splitter that has several "passbands," or no beam splitter. A multiple beam splitter can be coated at an angle, causing a variance in a thickness across a filter substrate, to compensate for wavelength shift with an angle. A beam splitter can be disposed at a low angle along a light or beam path to sharpen edges of the filtered light and can ease fabrication. A beam splitter can be disposed at a 45° angle of incidence along a light beam path. A low angle can include an angle of incidence less than 45°, less than 30°, or less than 15°. A multiple passband filter can be formed by coating different light interference materials over respective areas of a substrate used in a multiple passband filter manufacture.

A Rugate filter is an example of an interference coating based on the refractive index that varies continuously in a direction, for example, perpendicular or 45 degrees to the film plane. When the refractive index varies periodically within two extreme values, a minus filter with high transmittance on either side of the rejection band can be made. Periodic Rugate filters can be manufactured.

Rugate notch filters can use refractory metal oxides to achieve coatings with exceptional thermal and environmental stability. These filters can be used in place of other types of notch filters, particularly where durability and reliability are desired. Rugate notch filters are available from Barr Associates (Westford, Mass.). The Rugate notch filter can be used as edge filters and beam splitters. Filter sizes or shapes are not limitations for the Rugate notch filter. The Rugate notch filter can provide environmental and thermal stability, a broad operating temperature range, narrow rejection bands, variety of shapes & sizes, high throughput, low ripple, and/or a broad spectral range. More information is available from, for example, www.barr-associates-uk.com, www.barrassociates.com/opticalfilters.php.

Multiple-notch filters can be made, for example, with a measured blocking of O.D. 6 or better. Notch filters with this type of deep blocking level at the light wavelength can also afford high transmission close to the light line.

According to various embodiments, excitation levels can increase when multiple dyes spaced apart spectrally are irradiated with excitation beams. This can lead to less spectral crosstalk. The dye matrix, condition number, and/or deconvolution in a system can be improved. The increased excitation levels can provide higher signal levels. Higher signal levels can be seen during the utilization of dyes that emit in the "red" spectrum. The dynamic range of the system can be improved. The system can reduce the compensation for variation in the emission beam intensity for various dyes.

FIG. 9c depicts percent light transmission plotted versus wavelength. According to various embodiments, the bandpass filter can allow light corresponding to the "blue," "green," "yellow," "red," and "orange" markers to pass through. The regions or zones corresponding to the excitation light of the LEDs can be blocked. According to various embodiments, the bandpass filter can include a single bandpass filter, a series of bandpass filters capable of filtering the light from the LEDs, a multi-notch filter, or a Rugate filter.

FIG. 9d depicts a plot of relative emission intensity versus wavelength, expressed in nm, for the filtered light. FIG. 9d, in effect, provides a breakdown, by wavelength, of the light transmitted through the exemplary bandpass filter. As shown in FIG. 9d, the markers excited by the LEDs used in the example of FIGS. 9a through 9d emit light in the "blue," "green," "yellow," "red," and "orange" ranges of wavelengths. Before focusing the light signals thus filtered onto the detector array of a CCD, a dispersion element can be used, such as grating 28 shown in FIG. 1. The resulting image on the CCD can be similar to that depicted in FIGS. 2 and 3, with the addition of one or more dark zones corresponding to the blocked excitation light wavelengths. The existence of one or more dark zones, however, does not prevent the performance of multicomponenting to determine the intrinsic dye concentrations of each band in an electropherogram. TDI can be performed during data collection with the above-described system embodiments.

According to various embodiments, when irradiating multiple-channels with multiple color LEDs, the channels can be selectively masked in order to keep the light signals generated by the markers in each channel separate from one another. For example and as shown in FIGS. 10 and 11, in an embodiment where three channels 68a, 68b, 68c, are provided, each channel can be selectively masked with a mask 70 to create three windows 72a, 72b, and 72c, in the irradiation zone 67. The mask can be made of a metallized surface on a glass or fused silica plate that is disposed adjacent, for example, immediately above, the channels. The metal can be deposited in a controlled manner, for example, by photolithography methods, to cover the entire plate except in the areas forming the windows 72a, 72b, and 72c. Alternatively, windows can be cut out of an optically non-transparent plate, or a plate with windows can otherwise be formed as known to those skilled in the art.

As depicted in FIG. 11, the array 34 of a detector can be configured such that it is divided into three frames 74a, 74b, and 74c, respectively, corresponding to windows 72a, 72b, and 72c, allowing TDI to be effected on the charges generated by light signals detected through each respective window on a window-by-window basis. The number of wavelengths can correspond to the number of channels, or can be less than the number of channels. The mask 70 can be a single mask with multiple windows; or a series of masks, each mask corresponding to one or more channels. A device with any number of channels can be masked. According to various embodiments, each channel can pass through one or more excitation zones. Each excitation zone can be read by a corresponding detector or emissions from each exciation zone can pass through a corresponding detection zone.

FIG. 12a is a schematic cut-away representation of a portion of detector array 34 corresponding to frame 74a for detecting light passing through window 72a. As shown in FIG. 12a, each charge 76 corresponding to an analyte band moves in the migration direction M, and the charge packets on the detector array 34 are accumulated over an integration time. Charges can be accumulated for TDI by shifting the charges on the detector array in the migration direction M at a predetermined speed corresponding to the average speed of migration of the analyte bands, as suggested in FIG. 12a by the shifting movements depicted by reference numeral 78. Data can be collected from frame 74a from the top of the frame to the bottom of the frame. Some of the light can be blocked by the mask, causing a variable collection efficiency, as depicted by FIG. 12b. The integration of the accumulated charges can occur on a frame-by-frame basis as previously explained in relation to FIGS. 4, 5a, and 5b, the frame data being combined in a known manner to create an electropherogram. It is further possible, according to various embodiments, to abut the frames, that is, to eliminate any distance between them so as to combine the resulting images on detector array 34. According to various embodiments, the above-described arrangements can allow the separation and detection of light signals from multiple channels while permitting the simultaneous irradiation of those channels with multiple color irradiation sources. According to various embodiments, a single camera can be used to maintain a spatial separation of light signals from each masked channel, or one camera per channel can be used.

According to various embodiments, modulating optics useful for the electrophoresis arrangements described herein are disclosed in U.S. application Ser. No. 09/564,790, the contents of which are incorporated herein in their entirety by reference. For example, the modulating optics shown in FIG. 1 of U.S. patent application Ser. No. 09/564,790, using a cat's eye aperture of FIG. 24, can be useful in various electrophoresis arrangements as described herein.

According to various embodiments, an apparatus for detecting analytes in a sample can include means defining one or more channels therein having a detection zone; means for separating a sample into analytes migrating along the one or more channels, wherein the sample can include analytes and can be disposed in contact with a migration medium disposed within the one or more channels, wherein each analyte is detectable by the presence of a marker; means for irradiating the detection zone with non-coherent radiation, that can thereby excite markers responsive to the radiation and which markers can emit light signals indicative of corresponding analytes; means for detecting the light signals by collecting the light signals and producing corresponding charges; means for effecting a time delay integration of the charges produced by the light signals within a detector array by accumulating within the detector array the charges corresponding to light signals associated with at least one given analyte during an integration time of the at least one given analyte moving across the detection zone; means for reading the accumulated charges; and means for separating the analytes based on the accumulated charges that are read. Various embodiments of the above-described means have been substantially shown in and described with relation to FIGS. 1 through 12b.

According to various embodiments, the apparatus can include a sorting mechanism to affect flow cytometry, or fluorescence-activated cell sorting, of the detected components of the sample in the channel-defining member. The components can be cells, blood cells, nucleic acid sequences, or other biological sample components. The sorting mechanism can be located after the detection zone. The sorting mechanism can be located a suitable distance from the detection zone to allow sufficient time for determination of the composition of a component of the sample based on the detected charges received corresponding to the light signals associated with the at least one component of the sample. Based on the identification of the component, the component can be directed into one of two or more channels. All components of a certain composition, charge, or other identifying factor, can be directed into the same respective channel.

Figure 13A:
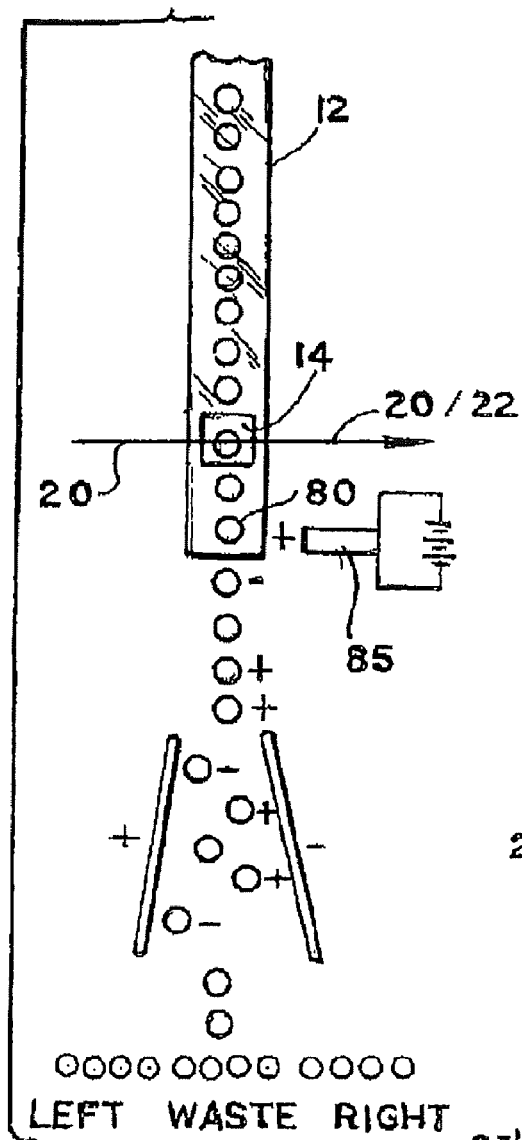
FIG. 13a is a schematic of a portion of an electrophoresis arrangement showing electrostatic sorting of the analytes or components, according to various embodiments.
Figure 13B:
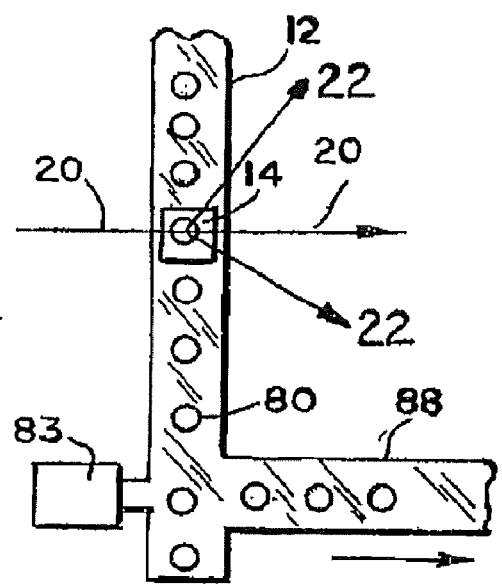
FIG. 13b is a schematic of a portion of an electrophoresis arrangement showing mechanical sorting of the analytes or components, according to various embodiments.
Figure 13C:
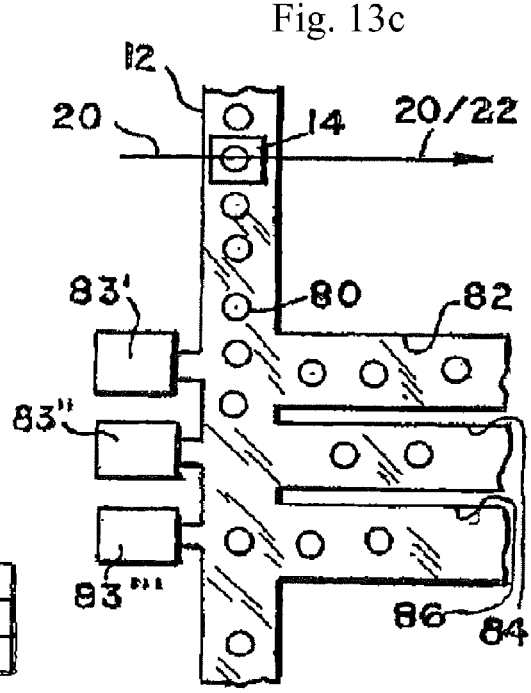
FIG. 13c is a schematic of a portion of an electrophoresis arrangement showing sorting of the analytes or components into various channels of a multi-channel microcard, according to various embodiments.

The sorting mechanism can include, for example, use of an electrostatic force, mechanical movement of respective channels, use of an acoustic pulse to divert the detected component to a respective channel, manipulation of electric field gradients, vacuum, or other means as known to those of ordinary skill in the art. Various examples of such methods of sorting are shown in FIGS. 13a-c. For example, FIG. 13a depicts a channel 12 including a detection zone 14 through which radiation 20 passes. Emission radiation signals 22 can emit along the same path as traveled by radiation 20, or along a separate path (not shown). Emission radiation signals 22 traveling along the same path as radiation 20 can be separated by using modulating optics as described herein. Emission radiation signals 22 can be detected, for example, by detection array 34 of FIG. 1 and FIG. 5a. An analyte or component 80 can travel via the channel 12 past the detection zone 14. A diverter, for example, a charge inducer 85 can be situated at a distance past the detection zone, sufficient for the detector to determine the composition or salient features of the component 80. The charge inducer 85 can apply a no charge, a negative charge, or a positive charge to the component or analyte 80. The component or analyte 80 having received a charge or no charge from the charge inducer 85 can pass out of channel 12 and travel towards one or more containers, for example, depicted as LEFT, WASTE, RIGHT in FIG. 13a. The one or more containers can correspond, for example, to a position directly below channel 12 for receipt of the non-charged components, to the left of the channel 12 for receipt of a charged component 80, and to the right of the channel 12 for receipt of an oppositely charged component 80. To direct the charged components 80, a magnetic field or electric field gradient can be applied across the area through which the components fall towards the containers. Negatively charged components can gravitate towards the positively charged side of the field, or a positively charged plate, and positively charged components can gravitate towards the negative side of the field or the negatively charged plate, being directed into their respective containers.

FIG. 13b depicts an alternate embodiment of a sorting mechanism. An analyte or component 80 can travel through a channel 12 having a detection zone 14 through which radiation 20 passes, emitting emitted light 22. Radiation 20 traveling along a direction before the detection zone 14 can continue traveling along the same direction after the detection zone 14 towards a detector (not shown). The detector and the detector's associated radiation modulating optics can be disposed transverse from the direction of the radiation 20, rather than along it. This transverse placement of the detector can improve detection of emitted light 22. Emitted light 22 can be detected in the presence of radiation 20. Emitted light 22 can be detected after separation from radiation 20. After passing through the detection zone 14, the component 80 can travel some distance before leaving the channel 12. The distance traveled can be related to the time necessary to determine the composition or salient features of the component having passed through the detection zone 14. The composition of the component can cause a diverter 83 to divert the component 80 to a branch channel 88 or continue flowing along the channel 12. The diverter 80 can allow detected component 80 to flow along channel 12. According to various embodiments, one or more mechanical arms having a collection tube, a collecting container, or other means of collecting the component, can be used to move into position below channel 12 to collect the designated component 80. A device to move a collection tube, for example, a series of mechanical arms, can be used to collect components of various natures, in different collection tubes. A waste container or collecting bin can be located below channel 12 to collect any components not placed in a container of one of the mechanical arms. According to various embodiments, the component can be removed from the stream of components leaving channel 12 into a desired branch channel 88 by some force, for example, an acoustic force, a vacuum force, a pneumatic force, or some other means of moving the particle out of the particle stream and into a designated container. According to various embodiments, a switchable electric field or varying current flow can be applied to or across the branch channel 88 using multiple electrodes, for example. The desired branch channel 88 can have a voltage potential across it, the other branch channels being allowed to "float" electrically. When a potential is present at the desired branch channel the analyte can flow into the intended branch channel. A movement of the detected component 80 into the electrically floating branch channels can be prevented. An analyte previously moved to a branch channel 88 can be prevented from moving into channel 12.

FIG. 13c is another embodiment of a sorting system. The particles 80 can travel in a channel 12 and pass through a detection zone 14. Channel 12 can be in communication with branch channels or side channels 82, 84, and 86, branching therefrom. After passing the detection zone 14, a component 80 can travel down channel 12 for a distance sufficient for analysis and recognition of the component 80 by the sorting system. The composition of the component 80 can be used to determine a side channel 82, 84, 86 for the component 80 to traverse. The component 80 can remain in the channel 12. Diverters 83', 83", and 83''' can be activated to divert component 80 into one of branch channels 82, 84, 86. The component 80 can be maneuvered into the correct or corresponding branch channel 82, 84, 86, or the component 80 can be allowed to continue along channel 12, by manipulation by electric field gradients, switchable electric fields, vacuum forces, a stream or air, or by other means of movement as known to those of ordinary skill in the art. In particular, the device illustrated in FIG. 13c can be part of a microdevice (not shown), for example, a microcard (not shown) containing channels 12, 82, 84, and 86 as microcapillaries.

According to various embodiments, a sorting mechanism can be activated upon detection of a component or analyte. The activation can cause a detection component to be removed from a flow stream containing the component. After a delay time, a diverter can direct the detection component to be removed from the flow stream into a container or a collection bin. According to various embodiments, any sample not directed to a container can be discarded as waste or can be used for sample recovery. According to various embodiments, one or more kinds of components can be present in the flow stream. One or more kinds of components can be detected. The diverter can direct variously identified/detection components into one or more containers. The diverter can employ a variety of methods to sort and/or collect components. The methods of sorting the components, also known as conducting flow cytometry or cytofluorometry, can include the use of motive forces, for example, electrostatic forces, mechanical movement, electric field gradients, switchable electric fields, vacuums, streams of air, or other motive forces as known to those of ordinary skill in the art. According to various embodiments, the containers collecting the components can be wells in a microdevice, for well, a microcard in microtiter format including one or more, for example, 24, 48, 96, 192, 384, or more, wells. A sorter suitable for component sorting, for example, cells, nucleotide acid sequences, can be obtained form DakoCytomation of Fort Collins, Colo. under the registered name MOFLO Sorters. Further background on flow cytometry and cell sorting can be obtained in, for example, Iloy, *Cell Sorting: Principles*, http://www.uwc-m.ac.uk/study/medicine/haema-tology/cytonetuk/documents/sort.pps (printed Apr. 14, 2004), which is incorporated herein its entirety by reference.

As shown with respect to FIGS. 13a-c, multiple methods of manipulating a component 80 for sorting the component based on its composition or based on other features, can be used after component 80 has passed detection zone 14. Flow cytometry can include coordination of the detector, the processor for analyzing the data received from the detector, and a control unit for controlling the motive force used to manipulate the movement of the component 80. The flow cytometer can include a control for receiving and acting on a control signal that is sent from a corresponding detector or time-delay integration system. Further description of optical flow cytometers can be found, for example, in U.S. Pat. No. 6,549,275 which is incorporated herein in its entirety by reference.

It is to be understood that various embodiments can be useful in detecting and imaging not only fluorescent labeled molecules, but also other chemical and/or biological cells or molecules, for example, proteins, viruses, and bacteria, nucleic acid sequences. Various embodiments can be useful for the detecting and imaging of components which can be electrophoretically or otherwise separated on a variety of carriers, for example, in capillary tubes, and across, on, in, or through slab gels, membranes, filter paper, Petri dishes, glass substrates, and the like.

According to various embodiments, the light source can be a Light Emitting Diode (LED). The LED can be, for example, an Organic Light Emitting Diode (OLED) an inorganic Light Emitted Diode, that can be polymer-based or small-molecule-based (organic or inorganic), an edge emitting diode (ELED), a Thin Film Electroluminescent Device (TFELD), or a Quantum dot based inorganic "organic LED." The LED can include a phosphorescent OLED (PHOLED). As used herein, the terms "excitation source," "irradiation source," and "light source" are used interchangeably.

According to various embodiments, excitation beams emitted from the light source can diverge from the light source at an angle of divergence. The angle of divergence can be, for example, from about 5° to about 75° or more. The angle of divergence can be substantially wide, for example, greater than 45°, yet can be efficiently focused by use of a lens, such as a focusing lens.

According to various embodiments, the light source can include one Light Emitting Diode (LED) or an array of LEDs. According to various embodiments, each LED can be a high power LED that can emit greater than or equal to about 1 mW of excitation energy. In various embodiments, a high power LED can emit at least about 5 mW of excitation energy. In various embodiments, the LED or array of LEDs can emit, for example, at least about 50 mW, at least about 500 mW, or at least about 1 W or more of excitation energy. A cooling device such as, but not limited to, a heat sink or fan, can be used with the LED. An array of high-powered LEDs can be used that draws, for example, upto about 10 watts of energy or more, upto about 100 watts of energy or more, or upto about 1000 watts of energy or more. The total power draw can depend on the power of each LED and the number of LEDs in the array. The use of an LED array can result in a significant reduction in power requirement over other light sources, such as, for example, a 75 watt halogen light source or a 150 watt halogen light source. Exemplary LED array sources are available, for example, from Stocker Yale of Salem, N.H. under the trade name LED AREALIGHTS, or from Lumileds Lighting, LLC of San Jose, Calif. under the trade name LUXEON, for example, a LUXEON STAR. Examples of LEDs can be found at http://www.lumileds.com/products/family.cfm?familyId=1. According to various embodiments, LED light sources can use about 1 milliwatt (mW) or more of power, for example, about 25 mW or more, about 50 mW or more, about 1 W or more, about 5 W or more, about 50W or more, or about 100 W or more, individually or when in used in an array.

According to various embodiments, a quantum dot can be used as a source for luminescence and as a fluorescent marker. Quantum dots can be used for both. The quantum dot based LED can be tuned to emit light in a tighter emission bandpass, for example, an emission bandpass including a full-width of half-max of about 10 nm or less, about 20 nm or less, or about 50 nm or less. The quantum dot based LED can increase the efficiency of the fluorescent system. The efficiency of a quantum dot based LED can theoretically be higher than that of conventional LEDs, potentially over 90% when sandwiched directly between two conductive films with each film directly touching each quantum dot as opposed to the present 20% efficiency for standard LEDs. Quantum dot based LEDs can be made utilizing a slurry of quantum dots, where current flows through an average of several quantum dots before being emitted as a photon. This conduction through several quantum dots can cause resistive losses in efficiency. Quantum dots can provide many more colors than conventional LEDs.

Quantum dots can be molecular-scale optical beacons. The quantum dot nanocrystals can behave like molecular LEDs (light emitting diodes) by "lighting up" biological binding events with a broad palette of applied colors. Quantum dots can provide many more colors than conventional fluorophores. Quantum dots can possess many other very desirable optical properties. Nanocrystal quantum dots can be covalently linked to biomolecules using standard conjugation chemistry. The quantum dot conjugate can then be used to detect a binding partner in a wide range of assays. According to various embodiments, streptavidin can be attached to quantum dots to detect biotinylated molecules in a variety of assays. Quantum dots can also be attached to antibodies and oligonucleotides. Any assay that currently uses, for example, fluorescent-tagged molecules, colorimetric enzymes, or colloidal gold, can be improved with quantum dot nanocrystal-tagged conjugates. An exemplary quantum dot implementation is available from Quantum Dot Corporation of Haywood, Calif. under the trademark QDOT. More information about quantum dots and their applications can be found at, for example, www.qdots.com, and in U.S. Pat. Nos. 6,207,229, 6,251,303, 6,306,310, 6,319,426, 6,322,901, 6,326,144, 6,426,513, and 6,444,143 to Bawendi et al., U.S. Pat. Nos. 5,990,479, 6,207,392, and 6,423,551 to Weiss et al., U.S. Pat. No. 6,468,808 to Nie et al., and U.S. Pat. No. 6,274,323 to Bruchez et al., which describe a variety of biological applications, methods of quantum dot manufacturing, and apparatuses for quantum dot nanocrystals and conjugates, all of which are incorporated herein by reference in their entireties.

Quantum dots can provide a versatile probe that can be used in, for example, in multiplex assays. Fluorescent techniques using quantum dot nanocrystals can be much faster than conventional enzymatic and chemiluminescent techniques, can reduce instrument tie-up, and can improve assay throughput. Colorimetric or detected reflectance techniques can be inferior to fluorescence and difficulties ensue when multiplex assays are developed based on these materials. Quantum dots can absorb all wavelengths "bluer" (i.e., shorter) than the emission wavelength. This capability can simplify the instrumentation required for multiplexed assays, since all different label colors can be excited with a single excitation source.

A Quantum dot based LED can emit light in an emission band that is narrower than an emission band of a normal LED, for example, about 50% narrower or about 25% narrower. The emission band of the quantum dots can be a function of the size distribution of the quantum dots, and thus can theoretically be extremely narrow. The Quantum dot based LED can also emit light at an electrical energy conversion efficiency of about, 90% or more, for example, approaching 100%. OLED films, including Quantum dot based LEDs, can be applied to a thermal block, used for heating and cooling samples, in a fluorescence system without interfering with the operation of the thermal block.

According to various embodiments, when an OLED is used, the OLED can have any of a variety of sizes, shapes, wavelengths, or combinations thereof. The OLED can provide luminescence over a large area, for example, to luminescence multiple sample wells. Scatter or cross-talk light between multiple sample wells for this single OLED can be reduced by either overlaying a mask on the OLED or by patterning the luminescent in the OLED to operatively align with the multiple sample wells. The OLED can be a low power consumption device. Examples of OLEDs in various configurations and wavelengths are described in, for example, U.S. Pat. No. 6,331,438 B1, which is incorporated herein by reference in its entirety. The OLED can include a small-molecule OLED and/or a polymer-based OLED also known as a Light-Emitting Polymer (LEP). A small-molecule OLED that is deposited on a substrate can be used. An OLED that is deposited on a surface by vapor-deposition technique can be used. An OLED can be deposited on a surface by, for example, silk-screening. An LEP can be used that is deposited by, for example, solvent coating.

According to various embodiments, an OLED is used and can be formed from one or more stable, organic materials. The OLED can include one or more carbon-based thin films and the OLED can be capable of emitting light of various colors when a voltage is applied across the one or more carbon-based thin films. Various LEDs can use different films, for example, quantum dot based LEDs, can use Indium tin oxide.

According to various embodiments, the OLED can include a film that is located between two electrodes. The electrodes can be, for example, a transparent anode, a metallic cathode, or combinations thereof. Several separate emission areas can be stimulated between a single set of electrodes where simultaneous illumination of the separate emission areas is required. According to such embodiments, only one power and control module might be required for several apparent light sources. The OLED film can include one or more of a hole-injection layer, a hole-transport layer, an emissive layer, and an electron-transport layer. The OLED can include a film that is about one micrometer in thickness, or less. When an appropriate voltage is applied to the film, the injected positive and negative charges can recombine in the emissive layer to produce light by means of electroluminescence. The amount of light emitted by the OLED can be related to the voltage applied through the electrodes to the thin film of the OLED. Various materials suitable for fabrication of OLEDs are available, for example, from H.W. Sands Corp. of Jupiter, Fla. Various types of OLEDs are described, for example, in U.S. Pat. No. 4,356,429 to Tang, U.S. Pat. No. 5,554,450 to Shi et al., and U.S. Pat. No. 5,593,788 to Shi et al., all of which are incorporated herein in their entireties by reference.

According to various embodiments, an OLED can be used and/or produced on a flexible substrate, on an optically clear substrate, on a substrate of an unusual shape, or on a combination thereof. Multiple OLEDs can be combined on a substrate, wherein the multiple OLEDs can emit light at different wavelengths. Multiple OLEDs on a single substrate or multiple adjacent substrates can form an interlaced or a non-interlaced pattern of light of various wavelengths. The pattern can correspond to, for example, a sample reservoir arrangement. One or more OLEDs can form a shape surrounding, for example, a sample reservoir, a series of sample reservoirs, an array of a plurality of sample reservoirs, or a sample flow path. The sample path can be, for example, a channel, a capillary, or a micro-capillary. One or more OLEDs can be formed to follow the sample flow path. One or more OLEDs can be formed in the shape of a substrate or a portion of a substrate. For example, the OLED can be curved, circular, oval, rectangular, square, triangular, annular, or any other geometrically regular shape. The OLED can be formed as an irregular geometric shape. The OLED can illuminate one or more sample reservoirs, for example, an OLED can illuminate one, two, three, four, or more sample reservoirs simultaneously, or in sequence. The OLED can be designed, for example, to illuminate all the wells of a corresponding multi-well array.

According to various embodiments, one or more excitation filters can be incorporated into the OLED substrate, thus eliminating additional equipment and reducing the amount of space needed for an optical system. For example, one or more filters can be formed in a layer of a substrate including one or more OLEDs and a layer including a sample flow path. The wavelength emitted by the OLED can be tuned by printing a fluorescent dye in the OLED substrate, as taught, for example, by Hebner et al. in "Local Tuning of Organic Light-Emitting Diode Color by Dye Droplet Application," APPLIED PHYSICS LETTERS, Vol. 73, No. 13 (Sep. 28, 1998), which is incorporated herein by reference in its entirety. When using multiple emission lines in an OLED, the OLED can be used in combination with a multiple notch emission filter.

According to various embodiments, an OLED can be substituted for an LED in any of the devices, systems, apparatuses, or methods described herein, wherein an LED is included or used. The OLED light source can have several OLED films stacked and operatively disposed such that several wavelengths of excitation beams can traverse the same optical path to illuminate the sample well. Several OLEDs forming excitation beams of the same wavelength can be stacked to provide higher output to illuminate the sample well.

According to various embodiments, an ELED can be substituted for an LED in any of the systems, devices, apparatuses, or methods described herein, wherein an LED is included or used. The ELED light source can be a light-emitting diode with output that emanates from between heterogeneous layers. An ELED can have greater radiance and coupling efficiency to an optical fiber or integrated optical circuit than a surface-emitting LED.

According to various embodiments, the light source can be a Solid State Laser (SSL) or a micro-wire laser. The SSL can produce monochromatic, coherent, directional light and can provide a narrow wavelength of excitation energy. The SSL can use a lasing material that is distributed in a solid matrix, in contrast to other lasers that use a gas, dye, or semiconductor for the lasing source material. Examples of solid state lasing materials and corresponding emission wavelengths can include, for example: Ruby at about 694 nm; Nd:Yag at about 1064 nm; Nd:YVO4 at about 1064 nm and/or about 1340 nm and which can be doubled to emit at about 532 nm or about 670 nm; Alexandrite at from about 655 nm to about 815 nm; and Ti:Sapphire at from about 840 nm to about 1100 nm. Micro-wire lasers are lasers where the wavelength of an excitation beam formed by the laser can be tuned or adjusted by altering the size of a wire. According to various embodiments, other solid state lasers known to those skilled in the art can also be used, for example, laser diodes. The appropriate lasing material can be selected based on the fluorescing dyes used, the excitation wavelength required, or both.

According to various embodiments, a Vertical Cavity Laser (VCL) can be used as an excitation source. A VCL can be substituted for an LED in any of the devices, systems, apparatuses, or methods described herein, wherein an LED is included or used. A VCL can be a type of surface-emitting laser diode that uses dielectric mirrors to produce surface emission. The laser cavity can be established in a vertical direction with respect to the plane of the active region. Examples, uses, and descriptions of VCL's can be found in U.S. Pat. No. 4,999,842, for example, that is incorporated herein in its entirety by reference.

If a SSL is used, the laser can be selected to closely match the excitation wavelength of a fluorescent dye. The operating temperature of the system can be considered in selecting an appropriate SSL. The operating temperature can be regulated or controlled to change the emitted wavelength of the SSL. The light source for the laser can be any source as known to those skilled in the art, such as, for example, a flash lamp. Useful information about various solid state lasers can be found at, for example, www.repairfaq.org/sam/lasersl.htm. Examples of solid state lasers used in various systems for identification of biological materials can be found in, for example, U.S. Pat. No. 5,863,502 to Southgate et al. and U.S. Pat. No. 6,529,275 B2 to Amirkhanian et al.; both of which are incorporated herein by reference in their entireties.

According to various embodiments, various types of light sources can be used singularly or in combination with other light sources. One or more OLEDs can be used with, for example, one or more non-organic LEDs, one or more solid state lasers, one or more halogen light sources, or combinations thereof.

According to various embodiments, an OLED layout can be connected to the power supply through leads arranged at opposite corners of the OLED layout. The power supply can include or be connected to one or more of a switch, a meter, an oscillator, a potentiometer, a detector, a signal processing unit, or the like. The OLED layout can include a plurality of individually addressable OLED lighting elements (not shown) with a separate lead connected to each lighting element. The wiring, leads, terminals, connection arms, and the like can be implemented in, for example, a substrate or a film. The OLED layout can be shaped to be aligned with, for example, a plurality of detection zones. Other embodiments of OLED layouts using various shapes and various numbers of well lamps are within the scope of the present teachings.

According to various embodiments, each individually addressable OLED lighting elements can include, for example, four individual lamps or OLED layers, capable of producing excitation wavelengths at four different frequencies.

The OLED layout can be constructed of a unitary or multi-part construction, of molded material, of stamped material, of screen printed material, of cut material, or the like.

Figure 14:
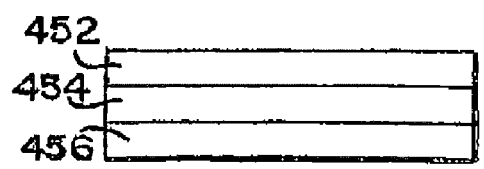
FIG. 14 illustrates an exemplary embodiment of a light source layout, for example, an organic light emitting diode (OLED) layout with varying color OLEDs stacked upon each other.

FIG. 14 illustrates an exemplary embodiment of a light source layout. An OLED layout 450 can include varying color OLEDs 452, 454, and 456 stacked upon each other. The layout can be useful for a compact light source design capable of forming excitation beams at varying wavelengths. The OLEDs 452, 454, and 456 can be transparent, allowing excitation beams from each OLED to pass through any other OLED so as to be directed towards a sample. The OLEDs 452, 454, and 456 can emit different colors, same colors, or a combination thereof depending on the color intensity and variety required. The OLEDs 452, 454, and 456 can share an electrode, for example, a cathode. One electrode, for example, an anode, for powering each of the OLEDs 452, 454, and 456 can be connected in electrical isolation from each respective anode to a control unit (not shown) if the capability to independently activate each of the OLEDs 452, 454, and 456 is desired. The OLEDs 452, 454, and 456 can electrically share one electrode, two electrodes, or no electrodes. Any number of OLEDs can be stacked, for example, two OLEDs, three OLEDs, four OLEDs, or more OLEDs, to form a light source, a respective light source, or an array of light sources.

According to various embodiments, multiple excitation wavelengths can be used to detect multiple sample components. According to various embodiments, the apparatus and method can be adapted for use by any suitable fluorescence detection system. For example, various embodiments of the apparatus and method can be used in a sequencing system with single or multiple samples, for example, in a nucleic acid sequence amplification reaction, in a sequencing detection system.

Various embodiments of the teachings are described herein. The teachings are not limited to the specific embodiments described, but encompass equivalent features and methods as known to one of ordinary skill in the art. Other embodiments will be apparent to those skilled in the art from consideration of the present specification and practice of the teachings disclosed herein. It is intended that the present specification and examples be considered as exemplary only.

What is claimed is:

1. A DNA sequencing system, comprising:
   a first detection zone;
   a second detection zone distinct from the first detection zone; and
   a plurality of TDI detectors which include at least a first TDI detector in communication with the first detection zone, the first TDI detector configured to detect at least one emission from at least one labeled analyte of a first wavelength or wavelength range from the first detection zone, and at least a second TDI detector in communication with the second detection zone, the second TDI detector configured to detect at least one emission from at least one labeled analyte of a second wavelength or wavelength range from the second detection zone, the first wavelength or wavelength range being different from the second wavelength or wavelength range,
   wherein the first and second TDI detectors detect distinct emissions.

2. The DNA sequencing system of claim 1, wherein the plurality of TDI detectors comprises a first, a second, a third, and a fourth TDI detector, each of the first, second, third, and fourth TDI detectors configured to detect emissions of a distinct wavelength or wavelength range.

3. The DNA sequencing system of claim 1, further comprising a first passband filter in communication with the first TDI detector, and a second passband filter in communication with the second TDI detector, the first passband filter configured to allow the first wavelength or wavelength range to be detected by the first TDI detector, and the second passband filter configured to allow the second wavelength or wavelength range to be detected by the second TDI detector.

4. The DNA sequencing system of claim 3, further comprising a multi-notch filter between at least one of the first and second detection zones and at least one of the TDI detectors.

5. The DNA sequencing system of claim 4, wherein the multi-notch filter is a rugate filter.

6. The DNA sequencing system of claim 1, further comprising a processor in communication with the plurality of TDI detectors, the processor configured to derive DNA sequence information of at least one polynucleotide sample from the emissions detected by the plurality of TDI detectors.

7. The DNA sequencing system of claim 1, wherein the emission of the first wavelength or wavelength range is indicative of a presence of at least a first nucleotide within the first detection zone, and the emission of the second wavelength or wavelength range is indicative of a presence of at least a second nucleotide within the second detection zone, the first nucleotide being different from the second nucleotide.

8. The DNA sequencing system of claim 1, further comprising a first and a second TDI detector in communication with the first detection zone, and a third and a fourth TDI detector in communication with the second detection zone, each of the first, second, third, and fourth TDI detectors configured to detect a distinct wavelength or wavelength range, each wavelength or wavelength range being indicative of a presence of a distinct nucleotide.

9. A DNA sequencing system, comprising:
   a first detection zone and a second detection zone, the first detection zone being distinct from the second detection zone; and
   a detection system having at least one TDI detector, the at least one TDI detector configured to detect at least one emission of a first wavelength or wavelength range from the first detection zone and at least one emission of a second wavelength or wavelength range from the second detection zone, the first wavelength or wavelength range being distinct from the second wavelength or wavelength range,
   wherein the first wavelength or wavelength range is indicative of a presence of a first type of nucleotide within the first detection zone and the second wavelength or wavelength range is indicative of a presence of a second type of nucleotide within the second detection zone, the first type of nucleotide being different from the second type of nucleotide.

10. The system of claim 9, wherein the first type of nucleotide is A, T, C, or G.

11. The system of claim 10, wherein the detection system includes at least four TDI detectors, each TDI detector configured to detect a distinct emission wavelength or wavelength range corresponding to a distinct type of nucleotide.

12. A DNA sequencing system, comprising:
    a first detection zone;
    a second detection zone distinct from the first detection zone; and
    a plurality of TDI detectors, at least one TDI detector configured to detect at least one emission from at least one labeled analyte of a first wavelength or wavelength range from the first detection zone, and at least one TDI detector configured to detect at least one emission from at least one labeled analyte of a second wavelength or wavelength range from the second detection zone, the first wavelength or wavelength range being different from the second wavelength or wavelength range,
    wherein the emission of the first wavelength or wavelength range is indicative of a presence of at least a first nucleotide within the first detection zone, and the emission of the second wavelength or wavelength range is indicative of a presence of at least a second nucleotide within the second detection zone, the first nucleotide being different from the second nucleotide.

13. A DNA sequencing system, comprising:
a first detection zone;
a second detection zone distinct from the first detection zone; and
a plurality of TDI detectors, at least one TDI detector configured to detect at least one emission from at least one labeled analyte of a first wavelength or wavelength range from the first detection zone, and at least one TDI detector configured to detect at least one emission from at least one labeled analyte of a second wavelength or wavelength range from the second detection zone, the first wavelength or wavelength range being different from the second wavelength or wavelength range,
wherein the plurality of detectors includes a first and a second TDI detector in communication with the first detection zone, and a third and a fourth TDI detector in communication with the second detection zone, each of the first, second, third, and fourth TDI detectors configured to detect a distinct wavelength or wavelength range, each wavelength or wavelength range being indicative of a presence of a distinct nucleotide.

* * * * *